(12) United States Patent
Kim et al.

(10) Patent No.: US 11,553,851 B2
(45) Date of Patent: Jan. 17, 2023

(54) METHOD FOR DETECTING BIOMETRIC INFORMATION BY USING SPATIAL LIGHT MODULATOR, ELECTRONIC DEVICE, AND STORAGE MEDIUM

(71) Applicant: Samsung Electronics Co., Ltd., Suwon-si (KR)

(72) Inventors: Jinho Kim, Suwon-si (KR); Seunghwan Shin, Suwon-si (KR); Junseok Oh, Suwon-si (KR); Inho Yun, Suwon-si (KR); Sunghwan Cho, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 211 days.

(21) Appl. No.: 17/042,529

(22) PCT Filed: Apr. 8, 2019

(86) PCT No.: PCT/KR2019/004133
§ 371 (c)(1),
(2) Date: Sep. 28, 2020

(87) PCT Pub. No.: WO2019/198991
PCT Pub. Date: Oct. 17, 2019

(65) Prior Publication Data
US 2021/0007617 A1    Jan. 14, 2021

(30) Foreign Application Priority Data
Apr. 12, 2018 (KR) .................. 10-2018-0042753

(51) Int. Cl.
*A61B 5/00* (2006.01)
*A61B 5/024* (2006.01)
*A61B 5/0295* (2006.01)

(52) U.S. Cl.
CPC ........ *A61B 5/02427* (2013.01); *A61B 5/0295* (2013.01); *A61B 5/681* (2013.01)

(58) Field of Classification Search
CPC .... A61B 5/02427; A61B 5/0295; A61B 5/681
See application file for complete search history.

(56) References Cited

U.S. PATENT DOCUMENTS

2014/0073899 A1    3/2014  Cohrs et al.
2016/0309068 A1    10/2016 Nadeau et al.
(Continued)

FOREIGN PATENT DOCUMENTS

| | | |
|---|---|---|
| JP | 2008-545515 A | 12/2008 |
| JP | 2017-505660 A | 2/2017 |
| WO | 2005/032360 A1 | 4/2005 |

*Primary Examiner* — Mark D Remaly
(74) *Attorney, Agent, or Firm* — Jefferson IP Law, LLP

(57) ABSTRACT

According to various embodiments, an electronic device may comprise: a housing comprising an inner space; a sensor structure positioned in the housing and exposed through a part of the housing, the sensor structure comprising a substantially transparent plate comprising a first surface facing away from the inner space and a second surface facing away from the first surface; a support structure positioned in the inner space so as to face the transparent plate; at least one light-emitting element mounted on the support structure while being spaced apart from the second surface and inserted between the second surface and the support structure; a spatial light modulator (SLM) disposed between the transparent plate and the LED while being spaced apart from the light-emitting element; a light-receiving element mounted on the support structure and positioned between the second surface and the support structure while being adjacent to a side surface of the light-emitting element; and a processing circuit comprising at least one electrical path electrically connected to the SLM, the processing circuit being operatively connected to the light- (Continued)

receiving element and configured to generate photoplethysmogram (PPG) data by using the light-emitting element. Other embodiments are possible.

15 Claims, 26 Drawing Sheets

(56) References Cited

U.S. PATENT DOCUMENTS

| | | |
|---|---|---|
| 2017/0164848 A1 | 6/2017 | Nadeau et al. |
| 2017/0231513 A1 | 8/2017 | Presura et al. |

SLM pattern (750)

PPG signal (770)

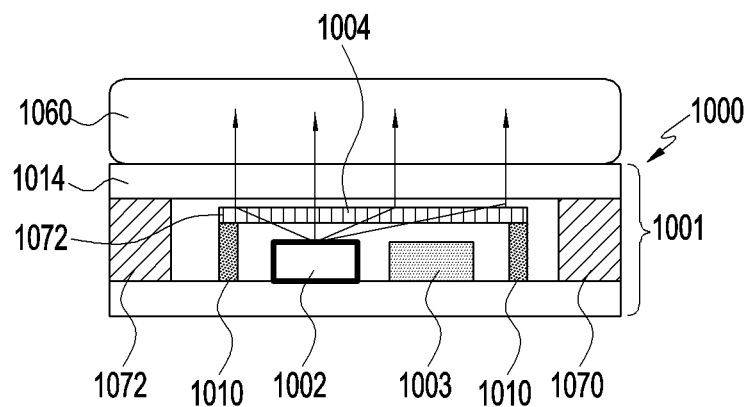
FIG.10C
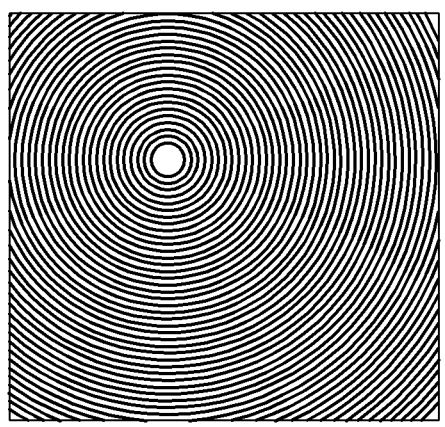 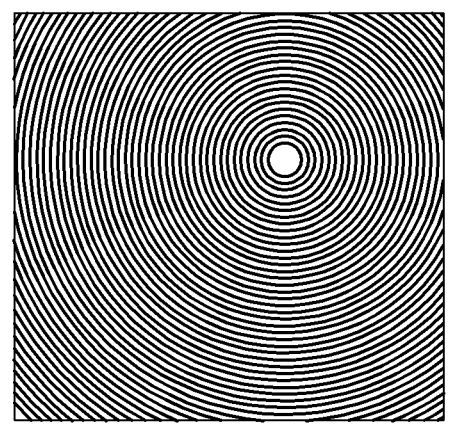
FIG.10D  FIG.10E

METHOD FOR DETECTING BIOMETRIC INFORMATION BY USING SPATIAL LIGHT MODULATOR, ELECTRONIC DEVICE, AND STORAGE MEDIUM

CROSS-REFERENCE TO RELATED APPLICATION(S)

This application is a National Phase Entry of PCT International Application No. PCT/KR2019/004133, which was filed on Apr. 8, 2019 and claims priority to Korean Patent Application No. 10-2018-0042753, which was filed on Apr. 12, 2018 in the Korean Intellectual Property Office, the contents of which are incorporated herein by reference.

BACKGROUND

1. Field

Various embodiments relate to: a method, an electronic device, and a storage medium for biometric information detection using a special light modulator.

2. Description of the Related Art

With a growing interest in health, various biometric information detection techniques have been developed. For example, photoplethysmography (PPG), among such biometric information detection techniques, is an optical technique that can be used to measure volumetric changes in the body. In photoplethysmography, the skin may be irradiated with light emitted from a light source so that a difference in light absorption due to a change in the volume of a blood vessel in the skin is expressed in the form of the intensity of reflected or transmitted light. Generally, blood flow in a blood vessel is changed not only by a heartbeat but also by physiological changes inside the body. Thus, a photoplethysmography (PPG) signal (also called PPG data) detected using photoplethysmography may be used to monitor a heart rate (HR), respiration, a stress level, blood pressure (BP), a blood flow rate, and a circulatory system state.

Conventionally, a pulse oximeter has been mainly used to measure PPG signals. However, recently, PPG signals have also come to be measured using mobile devices, such as a wrist-wearable device and a smart phone.

SUMMARY

A conventional simple irradiation-type PPG sensor cannot irradiate only a blood vessel with light but irradiates the entire skin with the light, and thus there is a need to increase a signal-to-noise ratio (SNR) in order to obtain useful biometric information of a user from an AC component of a PPG signal. For example, a field of view (FOV) of a light-emitting diode (LED) light-emitting element is about 2 mm×2 mm and the arteriole of a finger has a size of 200 microns, and thus, in the case where a light-emitting device of the PPG sensor is an LED light-emitting element, when the LED light-emitting element irradiates a user's skin with light, only about 10% of all light emitted by the LED light-emitting element reaches the user's blood vessel and the remaining 90% of the light reaches skin tissues, whereby noise components of an output signal of the PPG sensor (e.g., noise of a DC component and noise of a high-frequency (HF) component) may increase. For example, since the conventional simple irradiation-type PPG sensor directly irradiates a user's skin with light without modulating the light, only a small percentage (about 10%) of light may reach a blood vessel, and thus the SNR may be low. Further, for example, when the PPG sensor is not completely in contact with the skin, background noise due to reflection or an external light source may increase, and thus the SNR may be reduced.

Conventionally, in order to solve the problems with the simple irradiation-type PPG sensor, a passive light modulation element such as a lens or a waveguide, allowing emitted light to be focused on a desired portion, has been applied to the PPG sensor. However, in the case of the PPG sensor employing the lens or the waveguide, a movement path (direction and focal distance) of light is required to be predesignated during sensor design, whereby the PPG sensor may be vulnerable to artifacts due to motion of the body during PPG signal detection. For example, the PPG sensor employing the lens or the waveguide may not appropriately respond to a change in the position of the PPG sensor and/or a change in the position of a blood vessel. In fact, blood vessels in the skin are moved by a user's motion, and are also minutely changed by a heartbeat. Thus, in the PPG sensor employing the lens or the waveguide, a direction and a focal distance of a light-emitting device for light focusing may be continuously changed. When the PPG sensor employing the lens or the waveguide is implemented as a wearable device or is mounted to a wearable device, an error attributable to the worn state (loosely worn or tightly worn state) of the wearable device is required to be minimized for continuous measurement. However, it may be difficult to respond to a change in the distance between the wearable device and a blood vessel according to the worn state of the wearable device by using the PPG sensor employing the lens or the waveguide. For example, when the PPG sensor, implemented as a wearable device or mounted to a wearable device, measures a biometric information signal in the radial artery, the PPG sensor may not be accurately positioned toward the radial artery according to the worn state of the wearable device because of the characteristics of the wearable device, and thus a new type of noise may be generated. For example, the position of the PPG sensor, implemented as a wearable device or mounted to a wearable device, may be changed by blood vessel dilation or the like. In this case, an output waveform (e.g., absorption reflection waveform) of a PPG signal may be reversely expressed and thus signal analysis may become difficult, and noise may also be added and thus the wave form may be distorted.

Various materials coexist in a human skin, and blood vessels are present in the skin. The skin has an optical characteristic in which the reduced scattering coefficient ($\mu s'$) is about 10 to 100 times greater than the absorption coefficient ($\mu a$), and thus a scattering characteristic may mainly act on the transfer of light into the skin. Therefore, even if a lens or a waveguide is correctly designed, when a light-emitting device of a PPG sensor employing the lens or the waveguide emits light, the percentage of the light effectively reaching a user's blood vessel may be significantly reduced due to scattering in the skin, compared with focusing of light by wave propagation in air. When the light-emitting device of the PPG sensor employing the lens or the waveguide emits light, the focusing efficiency of the light actually reaching a blood vessel in a user skin is lower than an ideally designed value due to scattering of the light, which may limit an increase in the focusing efficiency of light reaching the blood vessel in the skin when using only the lens or the waveguide.

Human blood vessels constrict and dilate in order to maintain the body temperature according to an ambient temperature change. The blood vessels constrict in a cold environment in order to minimize heat loss though the blood vessels. The constriction of the blood vessels may hinder acquisition of an output signal having a good quality by a PPG sensor. When the size of a blood vessel is changed in response to a change in an external temperature, in the case of the conventional simple irradiation-type PPG sensor, emission of light onto a portion other than the blood vessel may increase, and thus the SNR may become poor, and in the case of the PPG sensor employing the lens or the waveguide, the probability of emission of light onto portions excluding the blood vessel may increase, and thus the SNR may become poor.

According to various embodiments, by applying a spatial light modulator (SLM) to a conventional PPG sensor or an electronic device capable of measuring a PPG signal so as to, when a light-emitting device irradiates a user's skin with light, increase the irradiation rate of light reaching a blood vessel in the skin and thereby increase a PPG signal quality, it is possible to provide a method, an electronic device, and a storage medium for biometric information detection using the spatial light modulator. The SLM may have a two-dimensional array and may actively modulate the property of light when an electrical signal is applied. For example, the SLM may modulate an amplitude and/or phase of light output from the light-emitting device by an electrical signal to adjust the direction of the light and suppress scattering of the light, and thus may increase the irradiation rate of the light in response to a continuously moving SLM pattern and may increase a signal-to-noise ratio (SNR) of a PPG signal.

According to various embodiments, when an SLM is applied to a conventional PPG sensor or an electronic device capable of measuring a PPG signal, and the PPG sensor or the electronic device capable of measuring a PPG signal is implemented as a wearable device or the PPG sensor is mounted to a wearable device, the PPG sensor or the electronic device may accurately find the position of a blood vessel (e.g., the radial artery) and may measure biometric information signals (e.g., radial artery blood pressure, etc.) corresponding to the blood vessel.

According to various embodiments, by disposing a partition wall of an electronic device capable of measuring a PPG signal or a PPG sensor under protective glass, flat window-type protective glass is applied to the electronic device, wherein an SLM is positioned above multiple light-emitting elements while leaving a space having a designated length (height) between the SLM and the multiple light-emitting elements so that the electronic device can perform light modulation control suitable for each of the multiple light-emitting elements. The electronic device may increase the linearity of light output from each of the multiple light-emitting elements by modulating the light through light modulation control suitable for each of the multiple light-emitting elements. Thus, crosstalk noise through the protective glass may be prevented.

According to various embodiments, an electronic device may include: a housing including an inner space; a sensor structure positioned in the housing and exposed through a part of the housing; and a processing circuit operatively connected to a light-receiving element and configured to generate photoplethysmogram (PPG) data by using the light-receiving element, wherein the sensor structure includes: a substantially transparent plate including a first surface facing a direction away from the inner space and a second surface facing a direction away from the first surface; a support structure positioned in the inner space while facing the transparent plate; at least one light-emitting element which is mounted on the support structure while being spaced apart from the second surface and which is inserted between the second surface and the support structure; a spatial light modulator (SLM) disposed between the transparent plate and the light-emitting element while being spaced apart from the light-emitting element; the light-receiving element, mounted on the support structure and positioned between the second surface and the support structure while being adjacent to a side surface of the light-emitting element; and at least one electrical path electrically connected to the SLM.

According to various embodiments, a method for biometric information detection using a spatial light modulator (SLM) of an electronic device may include: turning on at least one light-emitting element of the electronic device; controlling at least one pixel of the SLM of the electronic device such that the SLM outputs a first pattern by using light output from the light-emitting element; and generating photoplethysmogram (PPG) data by using a light-receiving element of the electronic device.

According to various embodiments, in a storage medium storing commands, the commands are configured to cause at least one circuit to perform at least one operation when the commands are executed by the at least one circuit, wherein the at least one operation may include: turning on at least one light-emitting element of an electronic device; controlling at least one pixel of a spatial light modulator (SLM) of the electronic device such that the SLM outputs a first pattern by using light output from the light-emitting element; and generating photoplethysmogram (PPG) data by using a light-receiving element of the electronic device.

In a method, an electronic device, and a storage medium for biometric information detection using a spatial light modulator, it is possible to: modulate a component of light output by the light-emitting device through an SLM by positioning the SLM above a light-emitting device in the structure of the electronic device including the light-emitting device and a light detection device; continuously measure a PPG signal of a blood vessel, the position of which is not fixed, through the light modulation; and enable the electronic device to be minimally affected by a change in an external environment, such as temperature, during PPG signal measurement.

In a method, an electronic device, and a storage medium for biometric information detection using a spatial light modulator, it is possible to: apply flat window-type protective glass to the electronic device by positioning an SLM above a light-emitting device in the structure of the electronic device including the light-emitting device and a light detection device; and thus solve problems related to waterproofing and/or aesthetic appearance of a conventional PPG sensor including a lens. For example, it is possible to increase the linearity of light output from a light-emitting element by disposing an SLM in the electronic device, and thus to reduce the generation of crosstalk noise. For example, multiple light-emitting elements and photodetectors can be disposed in a narrow area by applying an SLM to the electronic device. For example, the influence of misalignment due to process variation can be reduced by applying an SLM to the electronic device.

BRIEF DESCRIPTION OF THE DRAWINGS

FIG. 10C is a cross-sectional view of an electronic device according to various embodiments;

FIG. 10D illustrates an example of an SLM waveform according to various embodiments;

FIG. 10E illustrates an example of an SLM waveform according to various embodiments.

DETAILED DESCRIPTION

Figure 1:
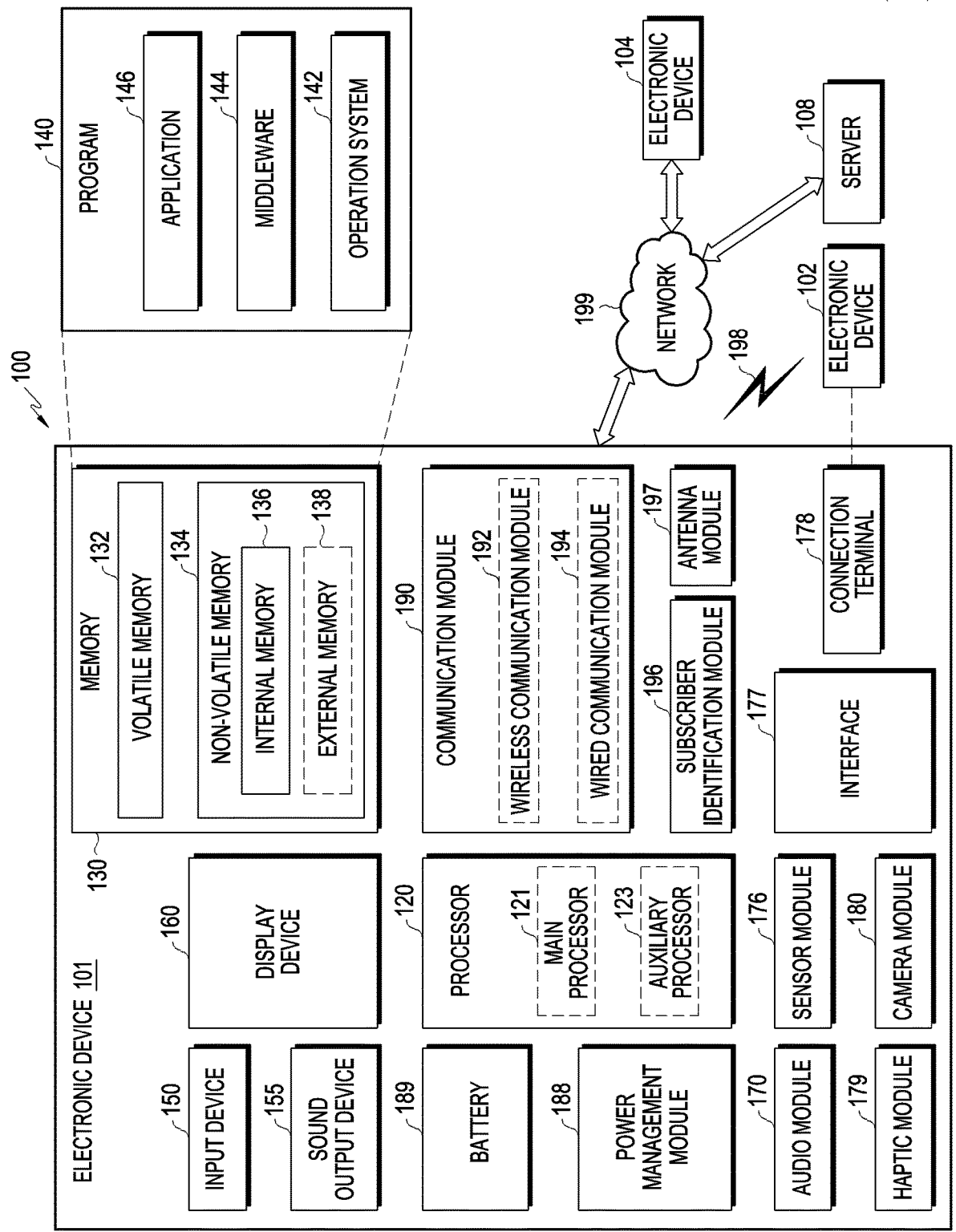
FIG. 1 is a block diagram of an electronic device in a network environment according to various embodiments.

FIG. 1 is a block diagram illustrating an electronic device 101 in a network environment 100 according to various embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control, for example, at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active (e.g., executing an application) state. According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by a component (e.g., the processor 120) of the electronic device 101, from the outside (e.g., a user) of the electronic device 101. The input device 150 may include, for example, a microphone, a mouse, or a keyboard.

The sound output device 155 may output sound signals to the outside of the electronic device 101. The sound output device 155 may include, for example, a speaker or a receiver. The speaker may be used for general purposes, such as playing multimedia or playing record, and the receiver may be used for incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or an external electronic device (e.g., an electronic device 102 (e.g., a speaker or a headphone)) directly or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image and moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and support a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include one or more antennas, and at least one antenna appropriate for a communication scheme used in the communication network, such as the first network 198 or the second network 199, may be selected, for example, by the communication module 190 from the one or more antennas. The signal or the power may then be transmitted or received between the communication module 190 and the external electronic device via the selected at least one antenna.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 2:
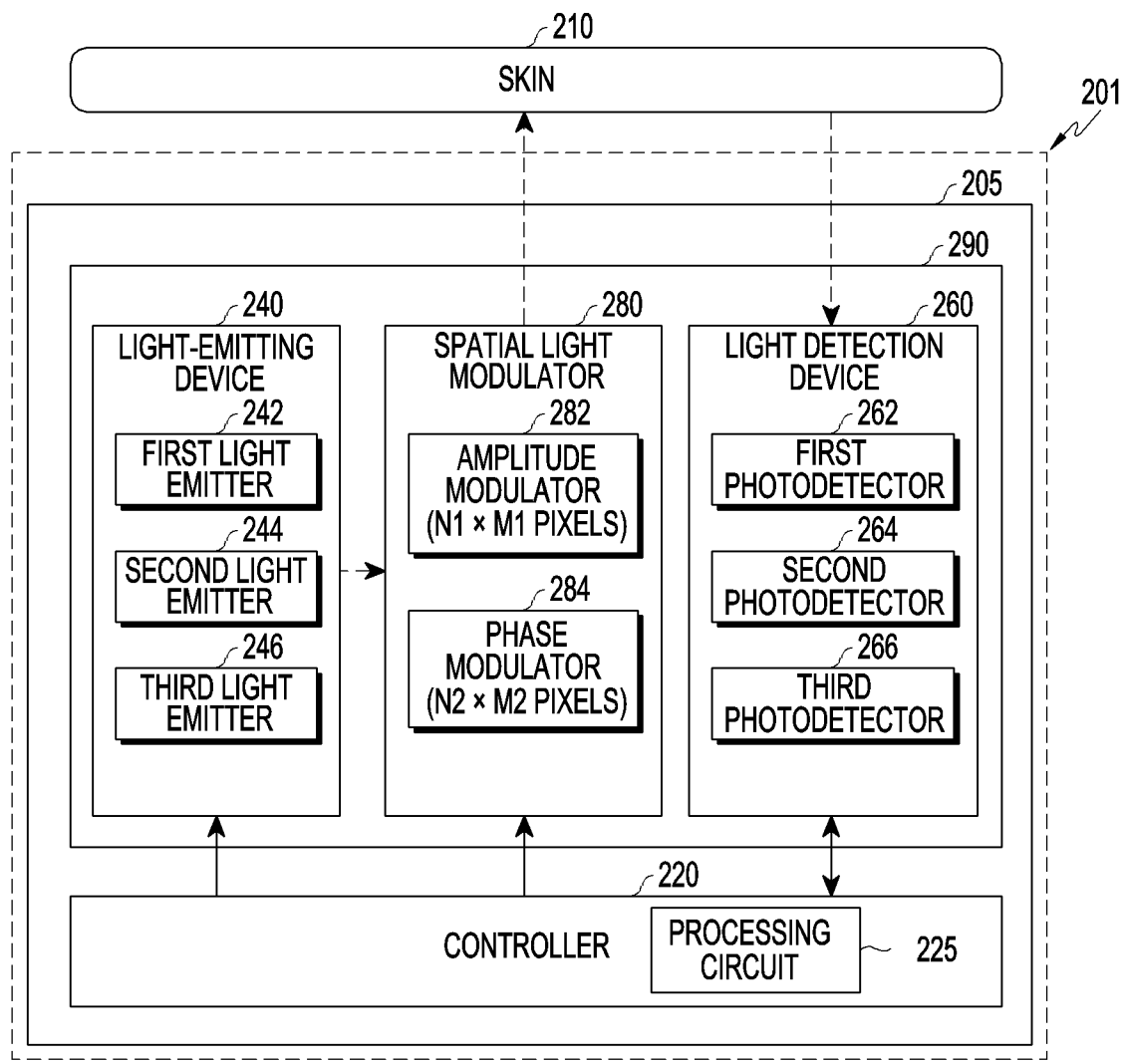
FIG. 2 is a block diagram of an electronic device according to various embodiments.

FIG. 2 is a block diagram of an electronic device according to various embodiments.

Referring to FIG. 2, an electronic device 201 may include a housing 205, a controller 220 (e.g., a processor 120), and a sensor structure 290 (also called a photoplethysmography (PPG) sensor).

According to one embodiment, the housing 205 may include an inner space, and the sensor structure 290, exposed through a part of the housing 205, may be positioned in the housing 205.

According to one embodiment, the sensor structure 290 may include a light-emitting device 240, a light detection device (also called a light-receiving device) 260, and a spatial light modulator (SLM) 280.

According to one embodiment, the light-emitting device 240 may be formed as a part for emitting light of one or more wavelengths. The light-emitting device 240 may be configured to generate light of one wavelength, or may be configured to complexly generate light of various wavelengths. The light-emitting device 240 may include at least one light-emitting element (light emitter). For example, the light-emitting device 240 may include a first light-emitting element 242, a second light-emitting element 244, and/or a third light-emitting element 246. For example, the light-emitting element may include a light-emitting diode, a laser diode (LD), a vertical-cavity surface-emitting laser (VCSEL), or a laser.

According to one embodiment, the light detection device 260 may include at least one photodetector (also called a light-receiving element), and may detect light reflected or scattered from a blood vessel in a user's skin 210. For example, the light detection device 260 may include a first photodetector 262, a second photodetector 264, and/or a third photodetector 266. For example, the first to third photodetectors 262, 264, and 266 may include a photodiode (PD), a single photon avalanche diode (SPAD), a complementary metal-oxide semiconductor (CMOS) array, a charge-coupled device (CCD) array, a lock-in pinned photodiode photodetector, or a photo multiplier tube.

The SLM 280 may have a two-dimensional array form in which the amplitude of light is changed and/or a two-dimensional array form in which the phase of light is changed. For example, the SLM 280 may include an amplitude modulator 282 and/or a phase modulator 284. For example, the amplitude modulator 282 and the phase modulator 284 may operate together or individually under control of the controller 220. The array size and pixel size (e.g., N1×M1 pixels) of the amplitude modulator 282 may be identical to the array size and pixel size (e.g., N2×M2 pixels) of the phase modulator 284, but may be different therefrom for a special purpose. When the amplitude modulator 282 is exclusively used, the characteristic of light is coherent or incoherent, but when the phase modulator 284 is used, the characteristic of light is coherent.

According to one embodiment, the controller 220 may be operably connected to the light detection device 260, and may include a processing circuit 225 configured to generate photoplethysmogram (PPG) data (also called a PPG signal) by using the light detection device.

According to one embodiment, when the light-emitting device 240 emits light onto the user's skin 210, a part of the light may reach a blood vessel in the user's skin 210, light changing in response to a change in blood flow may be absorbed, and a component of the remaining light may be reflected or scattered and may then reach the light detection device 260. Light that reaches the light detection device 260 may be output as an alternating-current (AC) component of a PPG signal. The AC component of the PPG signal is directly related to a change in blood flow through a blood vessel in the skin, and thus may be an important component (signal) indicating the characteristics of a circulatory system. For example, the shape of a PPG signal waveform and PPG signal quality may be important for the accuracy of pulse wave analysis (PWA) for analyzing blood pressure. However, the AC component of the PPG signal may exist together with a large direct-current (DC) component (e.g. noise) of light (e.g. background light) emitted by an external light source, which is not light that is absorbed and scattered by the skin excluding a blood vessel or is generated by the light-emitting device.

The processing circuit 225 may control the light-emitting device 240, the light detection device 260, and the SLM 280. For example, the processing circuit 225 may simultaneously control the light-emitting device 240 and the light detection device 260, and may control the SLM 280 while light is emitted from the light-emitting device 240 so as to change the form in which the light ultimately reaches the user's skin 210. For example, the light detection device 260 may sense, under the control of the processing circuit 225, light reflected from a blood vessel in the user's skin 210 to detect information (e.g. to generate photoplethysmogram data (measure a PPG signal)). For example, the processing circuit 225 may transfer a feedback signal to the SLM 280 on the basis of the information detected by using the light detection device 260.

Figure 3A:
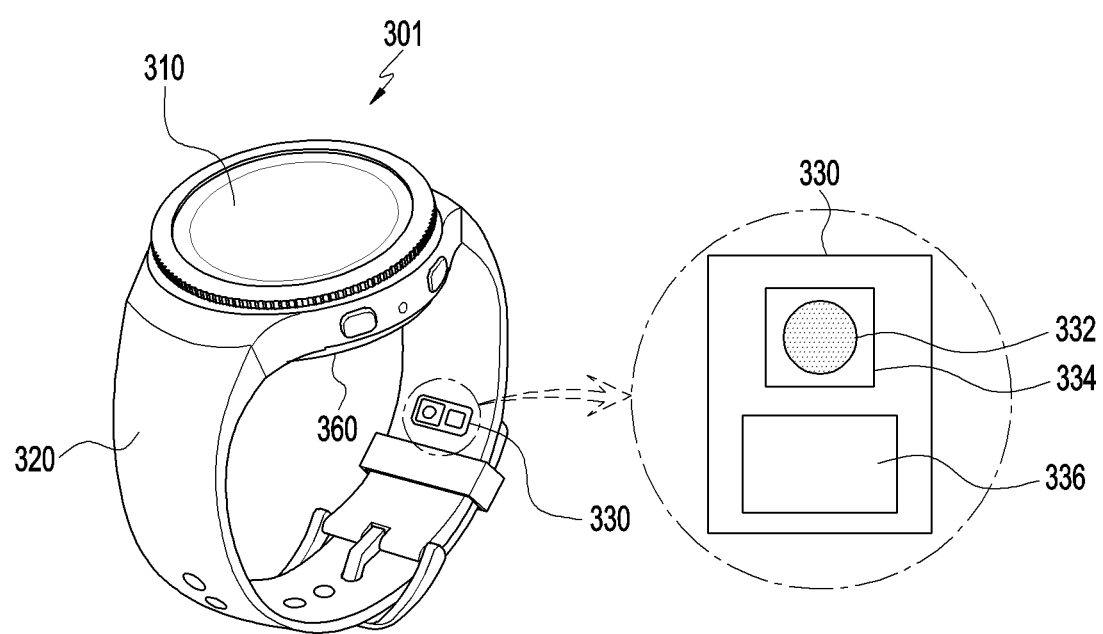
FIG. 3A illustrates an electronic device capable of measuring a PPG signal according to various embodiments.

FIG. 3A illustrates an electronic device capable of measuring a PPG signal according to various embodiments.

Referring to FIG. 3A, the electronic device 301 (e.g., the electronic device 201) may be a watch-type or band-type wearable electronic device. For example, the electronic device 301 may include a display 310 (e.g., the display device 160) and a band 320, and a PPG sensor 330 (e.g., the sensor structure 290) may be mounted (or disposed) on a first surface (e.g., the inner surface) of the band 320.

According to one embodiment, the PPG sensor 330 may include a light-emitting diode (LED) 332 (e.g., the first light-emitting element 242), an SLM 334 (e.g., the SLM 280), and a photodiode (PD) 336 (e.g., the first photodetector 262). For example, as illustrated in FIG. 3A, the SLM 334 may be disposed above the LED 332, and the PD 336 may be disposed adjacent to the LED 332.

Figure 3B:
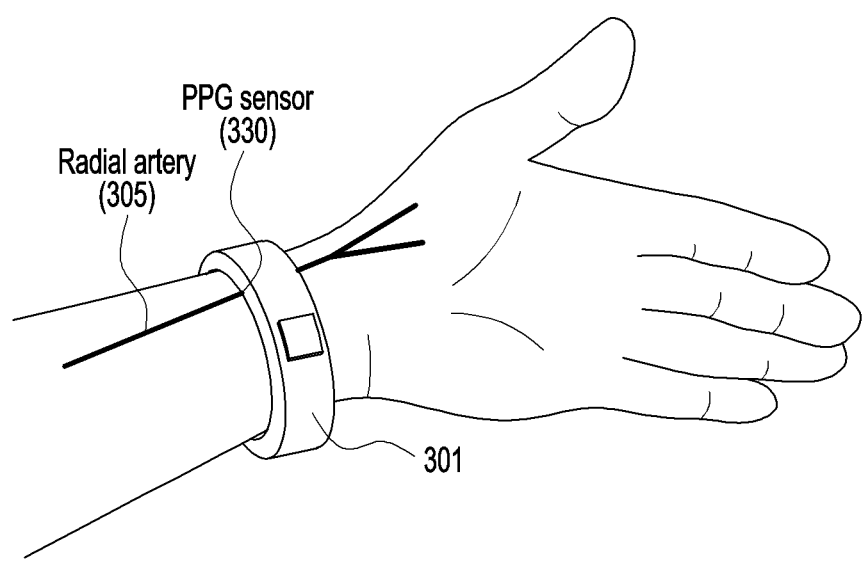
FIG. 3B is a view for describing the arrangement of a PPG sensor in an electronic device according to various embodiments.

FIG. 3B is a view for describing the arrangement of a PPG sensor in an electronic device according to various embodiments. For example, as illustrated in FIG. 3B, the PPG sensor 330 may be disposed at a portion of the wearable electronic device 301 such that the PPG sensor 330 is positioned near the radial artery 305 of a user's wrist when the user wears the electronic device 301 on the wrist.

The mounting position of the PPG sensor 330 in the electronic device 301 in the above-described embodiment of FIG. 3A is one example. The mounting position of the PPG sensor 330 in the electronic device 301 may be changed depending on whether the watch-type or band-type wearable electronic device is manufactured for a left-handed person or a right-handed person. For example, the PPG sensor 330 may be mounted on the rear surface 360 of the electronic device.

In the above-described embodiment of FIG. 3A, a description has been made of the case where the PPG sensor 330 has one LED 332. However, multiple LEDs 332 with various wavelength bands may be applied to the PPG sensor 330.

In the above-described embodiment of FIG. 3A, a description has been made of the case where the PPG sensor 330 has one PD 336. However, multiple PDs 336 may be applied to the PPG sensor 330, and the PD 336 may be implemented in various forms.

In the above-described embodiment of FIG. 3A, the electronic device 301 having the PPG sensor 330 mounted thereto has been described as a watch-type or band-type wearable electronic device. However, the electronic device 301 may take various other forms, including those of a wearable device (e.g., glasses, a necklace, or earbuds), an Internet-of-Things (IOT) device, and a mobile device, and the PPG sensor 330 may also be mounted at various positions. For example, when the electronic device 301 is a mobile device, the PPG sensor 330 may be mounted at various positions such as beside a camera of the electronic device 301.

Figure 4A:
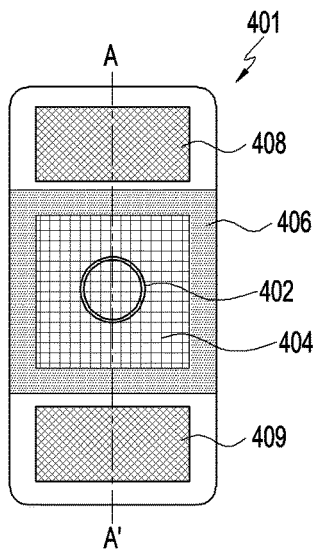
FIG. 4A is a plan view illustrating main elements of an electronic device according to various embodiments.
Figure 4B:
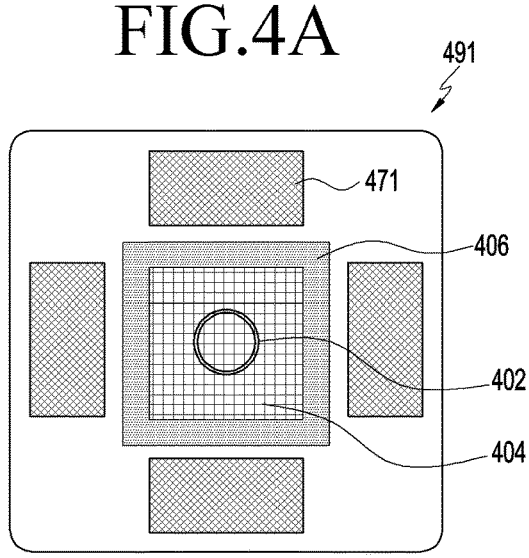
FIG. 4B is a plan view illustrating main elements of an electronic device according to various embodiments.
Figure 4C:
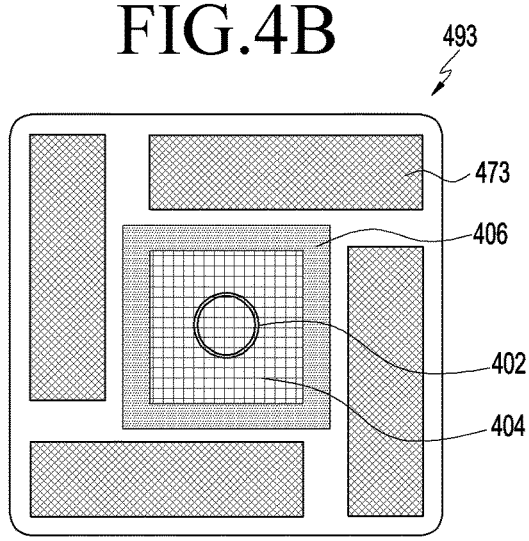
FIG. 4C is a plan view illustrating main elements of an electronic device according to various embodiments.
Figure 4D:
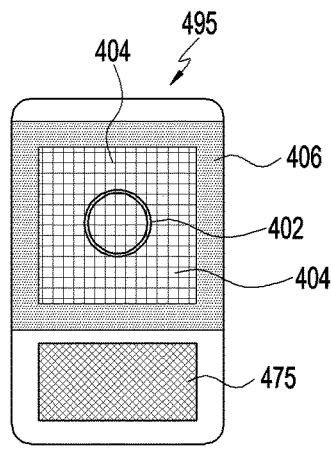
FIG. 4D is a plan view illustrating main elements of an electronic device according to various embodiments.
Figure 4E:
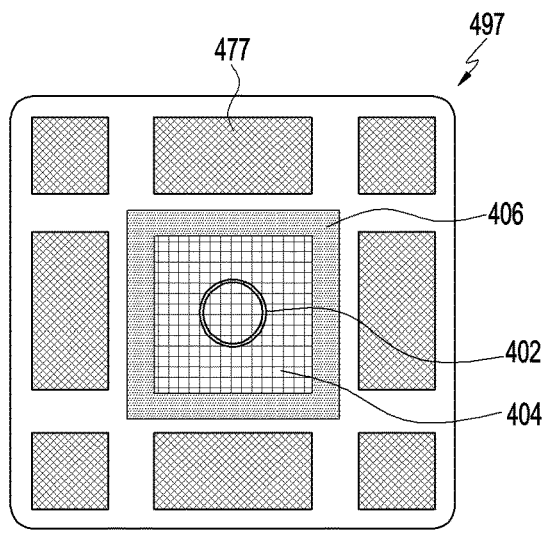
FIG. 4E is a plan view illustrating main elements of an electronic device according to various embodiments.
Figure 4F:
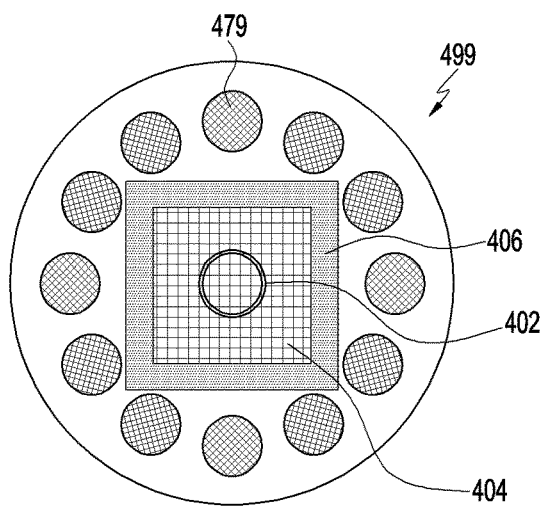
FIG. 4F is a plan view illustrating main elements of an electronic device according to various embodiments.

FIG. 4A is a plan view illustrating main elements of an electronic device according to various embodiments. FIG. 4B is a plan view illustrating main elements of an electronic device according to various embodiments. FIG. 4C is a plan view illustrating main elements of an electronic device according to various embodiments. FIG. 4D is a plan view illustrating main elements of an electronic device according to various embodiments. FIG. 4E is a plan view illustrating main elements of an electronic device according to various embodiments. FIG. 4F is a plan view illustrating main elements of an electronic device according to various embodiments.

Referring to FIGS. 4A to 4F, each of electronic devices 401, 491, 493, 495, 497, and 499 (e.g., the electronic device 301) may include a first light-emitting element 402 (e.g., the first light-emitting element 242), an SLM 404 (e.g., the SLM 280), a partition wall (or a light-blocking wall) 406, and at least one photodetector 408, 409, 471, 473, 475, 477, or 479 (e.g., the first photodetector 262, the second photodetector 264, and/or the third photodetector 266). For example, the light-emitting element 402 may be an LED, and the at least one photodetector may be a PD.

According to one embodiment, as illustrated in FIGS. 4A to 4F, in order to modulate light output from the light-emitting element 402, the SLM 404 may be disposed above the light-emitting element 402 so as to cover the entire light-emitting element 402. The SLM 404 and the light-emitting element 402 may be disposed in the state of being surrounded by the partition wall 406 such that the light output from the light-emitting element 402 can be emitted to the outside only through the SLM 404.

According to one embodiment, the at least one photodetector 408 may be disposed adjacent to the partition wall 406.

Referring to FIG. 4A, the electronic device 401 may include two photodetectors 408 and 409, and the two photodetectors 408 and 409 may be disposed at both sides of the partition wall 406, respectively (or in a structure surrounding both sides, respectively). For example, the two photodetectors 408 and 409 may have the same form.

Referring to FIG. 4B, the electronic device 491 may include four photodetectors 471, and the four photodetectors 471 may be disposed so as to at least partially surround four side surfaces of the partition wall 406. For example, the four photodetectors 471 may have the same form.

Referring to FIG. 4C, the electronic device 493 may include four photodetectors 473, and the four photodetectors 473 may be disposed so as to at least partially surround four side surfaces of the partition wall 406. For example, the four photodetectors 473 may have the same form.

Referring to FIG. 4D, the electronic device 495 may include one photodetector 475, and the photodetector 475 may be disposed at one side surface of the partition wall 406.

Referring to FIG. 4E, the electronic device 497 may include eight photodetectors 477, and the eight photodetectors 477 may be disposed so as to at least partially surround four surfaces and corners of the partition wall 406. For example, some of the eight photodetectors 477 may have the same form, and others thereof may have different forms.

Referring to FIG. 4F, the electronic device 499 may include multiple photodetectors 479, and the multiple photodetectors 479 may be disposed in an annular shape surrounding the partition wall 406. For example, the multiple photodetectors 479 may have the same form.

According to one embodiment, under the control of a processing circuit (e.g., the processing circuit 225), the SLM 404 may control (change) the direction of light output from the light-emitting element 402 so that the light can be emitted to the outside in a desired direction. Thus, when photodetectors are provided at all positions to which light emitted from the light-emitting element 402 may be directed, the accuracy of reception of a signal by each of the photodetectors 408, 409, 471, 473, 475, 477, and 479 may be increased.

According to one embodiment, when light is emitted in a specific direction under the control of a processing circuit (processing circuit 225), the electronic device 401 of FIG. 4A may use a detector, positioned in the direction in which the light is emitted among two detectors 408 and 409, as a main detector, and may not use the remaining detector in order to reduce power consumption, or may use the remaining detector as a background-noise-sensing device (e.g. an ambient light sensor).

The above-described embodiments of FIGS. 4A to 4F illustrate examples in which one light-emitting element 402 is provided. However, according to another embodiment, multiple light-emitting elements 402 may be provided. For example, one SLM 404 may be disposed above multiple light-emitting elements 402 so as to cover the multiple light-emitting elements 402, and the multiple light-emitting elements 402 may be disposed in the state of being surrounded by the partition wall 406.

Figure 5:
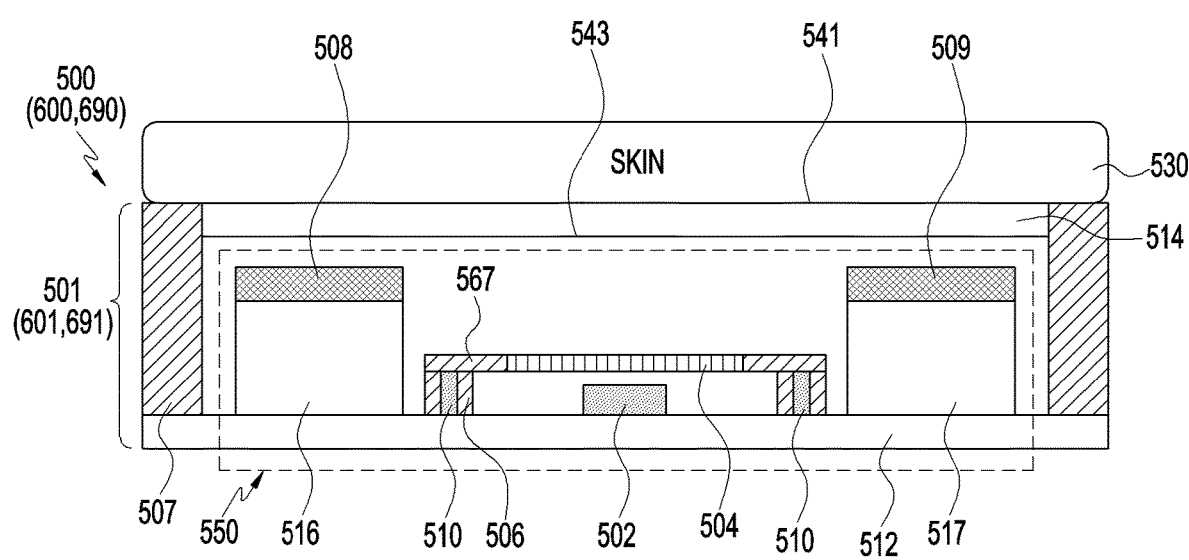
FIG. 5 is a cross-sectional view of an electronic device according to various embodiments.

FIG. 5 is a cross-sectional view of a sensor structure of an electronic device according to various embodiments.

Referring to FIG. 5, a sensor structure 501 (e.g., the sensor structure 290) (e.g. sensor structures 601 and 609) of an electronic device 500 (e.g., the electronic device 201) (e.g., the electronic devices 600 and 690) may include a light-emitting element 502 (e.g., the first light-emitting element 242), an SLM 504 (e.g., the SLM 280), a first partition wall 506, a second partition wall 507, one or more photodetectors 508 and 509 (e.g., the first photodetector 262 and/or the second photodetector 264), at least one connection pin 510, a support structure 512, a transparent plate (also called protective glass) 514, and/or one or more interposers 516 and 517.

According to one embodiment, FIG. 5 is a cross-sectional view taken along line A-A' of the electronic device 401 in FIG. 4A. For example, the electronic device 500 may be the electronic device 401 of FIG. 4A, the light-emitting element 502 of the sensor structure 501 may be the light-emitting element 402 of FIG. 4A, the SLM 504 may be the SLM 404 of FIG. 4A, the partition wall 506 may be the partition wall 406 of FIG. 4A, and the one or more photodetectors 508 and 509 may be the two photodetectors 408 and 409 of FIG. 4A.

According to one embodiment, the transparent plate 514 may include: a first surface 541 facing a direction away from the inner space included in a housing of the electronic device 500; and a second surface 543 facing a direction away from the first surface.

According to one embodiment, the support structure 512 may include a printed circuit board (PCB).

According to one embodiment, the light-emitting element 502 may be disposed on the support structure 512, and the support structure 512 may be electrically connected to the light-emitting element 502. For example, a processing circuit (e.g., the processing circuit 225) may transfer a control signal to the light-emitting element 502 via a wire. The SLM 504 may be disposed between the light-emitting element 502 and a skin 530. The SLM 504 may be connected to the support structure 512 through the connection pin 510, and the state of each pixel of the SLM 504 may be changed according to a control signal from the processing circuit (e.g., the processing circuit 225). The connection pin 510 may be coupled to the first partition wall 506 disposed on the support structure 512, and may be formed to support the SLM 504. For example, the connection pin 510 may be an electrical path through which a control signal from the processing circuit is transferred. Since the SLM 504 is surrounded by the first partition wall 506, light output from the light-emitting element 502 may be blocked such that the light cannot be emitted to the outside until the light is modulated through the SLM 504. For example, the SLM 504 may be formed of one layer, and may be an amplitude modulator or a phase modulator. In another example, the SLM 504 may be formed of two layers, and an amplitude modulator and a phase modulator may coexist. A space having a designated height may be formed between the light-emitting element 502 and the SLM 504. For example, a space may be formed between the light-emitting element 502 and the SLM 504 according to the length (or height) of the connection pin 510 (and/or the first partition wall 506). A space having a designated height may be formed between the SLM 504 and the transparent plate 514 such that the direction of light is scanned by the SLM 504. For example, as illustrated in FIG. 5, a space may be formed between the SLM 504 and the transparent plate 514 according to the length (or height) of the second partition wall 507 supporting the transparent plate 514. For example, the distance (or necessary space) between the SLM 504 and transparent plate 514 may be determined by the maximum angle, at which scanning can be performed by the SLM 504, and by the maximum scanning distance required on the skin. For example, the distance between the SLM 504 and the transparent plate 514 may be obtained by Equation 1 below.

$$\text{Distance between the SLM 504 and the transparent plate 514} = \text{skin scanning distance}/\tan(\text{max SLM angle}) \quad \text{[Equation 1]}$$

One or more photodetectors 508 and 509 capable of sensing components of light returning from a blood vessel in a user's skin 530 may be disposed near the light-emitting element 502. The one or more photodetectors 508 and 509 may be disposed between the first partition wall 506 and the second partition wall 507, and a space having a designated height may be formed between the photodetector 508 and the transparent plate 514. One or more interposers 516 and 517 may be disposed between the first partition wall 506 and the second partition wall 507 on the top of the support structure 512. One or more photodetectors 508 and 509 may be disposed on the tops of the one or more interposers 516 and 517, respectively. For example, the support structure 512 may be electrically connected to the one or more photodetectors 508 and 509 through via holes formed in the one or more interposers 516 and 517 or conductors with which the via holes are filled, or the support structure 512 may be electrically connected to the one or more photodetectors 508 and 509 through another wire. For example, the one or more interposers 516 and 517 may be insulative.

For example, in order to reduce noise which enters the one or more photodetectors 508 and 509 because light modulated by the SLM 504 is directly reflected through the transparent plate 514, the one or more photodetectors 508 and 509 may be disposed close to the transparent plate 514 by raising the heights thereof by using the one or more interposers 516 and 517.

In the above-described embodiment of FIG. 5, a description has been made of an example in which one light-emitting element 502 is provided. However, according to another embodiment, multiple light-emitting elements 502 may be provided. For example, one SLM 504 may be disposed above multiple light-emitting elements 502 so as to cover the multiple light-emitting elements 502, and the multiple light-emitting elements 502 may be disposed in the state of being surrounded by the partition wall 506.

In the above-described embodiment of FIG. 5, a description has been made of the case where a space is formed between the SLM 504 and the transparent plate 514. However, according to another embodiment, the SLM 504 and the transparent plate 514 may be in close contact with each other, without any space therebetween. For example, the SLM 504 may be attached to the transparent plate 514.

According to various embodiments, an electronic device (e.g., the electronic device 201) may include: a housing (e.g., the housing 205) including an inner space; and a sensor structure (e.g., the sensor structure 290 or 501) positioned in the housing and exposed through a part of the housing. The sensor structure may include: a substantially transparent plate (e.g. the transparent plate 514) including a first surface (e.g., the first surface 541) facing a direction away from the inner space and a second surface (e.g., the second surface 543) facing a direction away from the first surface; a support structure (e.g., the support structure 512) positioned in the inner space while facing the transparent plate; at least one light-emitting element (e.g., the light-emitting element 502), which is mounted on the support structure while being spaced apart from the second surface and which is inserted between the second surface and the support structure; a spatial light modulator (SLM) (e.g., the SLM 504) disposed between the transparent plate and the light-emitting element while being spaced apart from the light-emitting element; a light-receiving element (e.g., the photodetector 508) mounted on the support structure and positioned between the second surface and the support structure while being adjacent to a side surface of the light-emitting element; and at least one electrical path (e.g., the connection pin 510) electrically connected to the SLM. The electronic device may include a processing circuit (e.g., the processing circuit 225) operatively connected to the light-receiving element and configured to generate photoplethysmogram (PPG) data by using the light-receiving element.

According to various embodiments, the light-emitting element may include a light-emitting diode (LED), a laser diode (LD), a vertical-cavity surface-emitting laser (VCSEL), or a laser.

According to various embodiments, the light-receiving element may include a single photon avalanche diode (SPAD), a complementary metal-oxide semiconductor (CMOS) array, a charge-coupled device (CCD) array, a lock-in pinned photodiode photodetector, or a photo multiplier tube.

According to various embodiments, the light-receiving element may include a light-receiving surface, and the light-emitting element may have a light-emitting surface.

According to various embodiments, the light-receiving surface is closer to the second surface than the light-emitting surface is.

According to various embodiments, the light-receiving surface is closer to the second surface than the SLM is.

According to various embodiments, the SLM may be spaced apart from the second surface, and the SLM may be configured to modulate at least one of the amplitude or phase of light emitted from the light-emitting element.

According to various embodiments, the light-emitting element may be configured to emit light having a wavelength.

According to various embodiments, the support structure may include a printed circuit board (PCB), and the electrical path may be connected to the printed circuit board.

According to various embodiments, the electronic device may further include at least one light-receiving element (e.g. the photodetector 509) mounted on the support structure and positioned between the second surface and the support structure while being adjacent to a side surface of the light-emitting element.

According to various embodiments, the electronic device may further include a partition wall (light block) (e.g., the first partition wall 506) mounted on the support structure and positioned between the light-emitting element and the light-receiving element, wherein a first surface 567 of the partition wall may be positioned under the second surface.

According to various embodiments, the processing circuit may generate the PPG data by using the light-receiving element while controlling at least one pixel of the SLM such that the SLM outputs a first pattern.

According to various embodiments, the processing circuit may: perform control, based on the first pattern, such that at least one pixel, among pixels of the SLM, outputs first light having a first amplitude or a first phase; identify a first pixel related to light to be scattered among the at least one pixel; and perform control such that the first pixel outputs second light having a second amplitude or a second phase.

According to various embodiments, the processing circuit may perform a random search for at least some of the SLM pixels, and may identify the first pixel, among the at least one pixel, based on a result of the random search.

According to various embodiments, the processing circuit may: perform control such that the at least one pixel among the pixels of the SLM outputs the first light having the first amplitude or the first phase, based on a magnitude of an AC component of a PPG signal wave included in the PPG data; identify the first pixel related to the light to be scattered among the at least one pixel; and perform control such that the first pixel outputs the second light having the second amplitude or the second phase.

According to various embodiments, the processing circuit may: control the at least one pixel of the SLM such that the SLM outputs a shifted pattern of the first pattern; and generate new PPG data by using the light-receiving element while the SLM outputs the shifted pattern.

According to various embodiments, the processing circuit may: control the at least one pixel of the SLM such that the SLM outputs a pattern obtained by adding a phase gradient to the first pattern; and generate new PPG data by using the light-receiving element while the SLM outputs the pattern including the added phase gradient.

According to various embodiments, the SLM may be attached to the transparent plate.

Figure 6A:
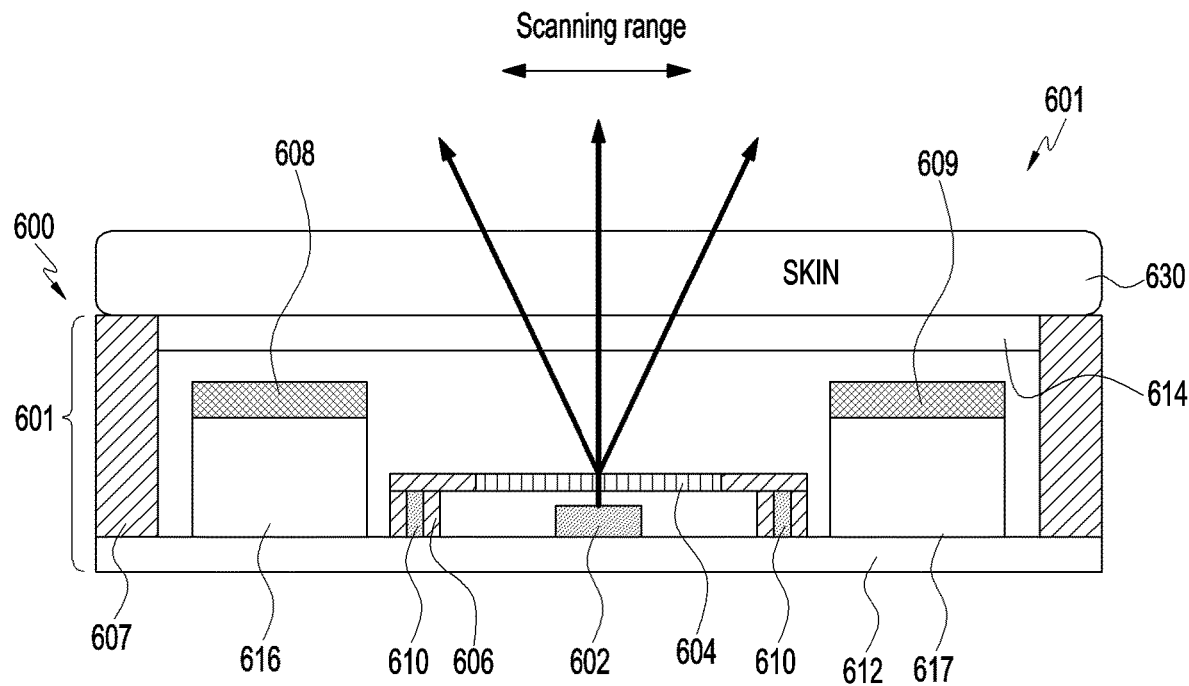
FIG. 6A is a cross-sectional view of a sensor structure of an electronic device according to various embodiments.
Figure 6B:
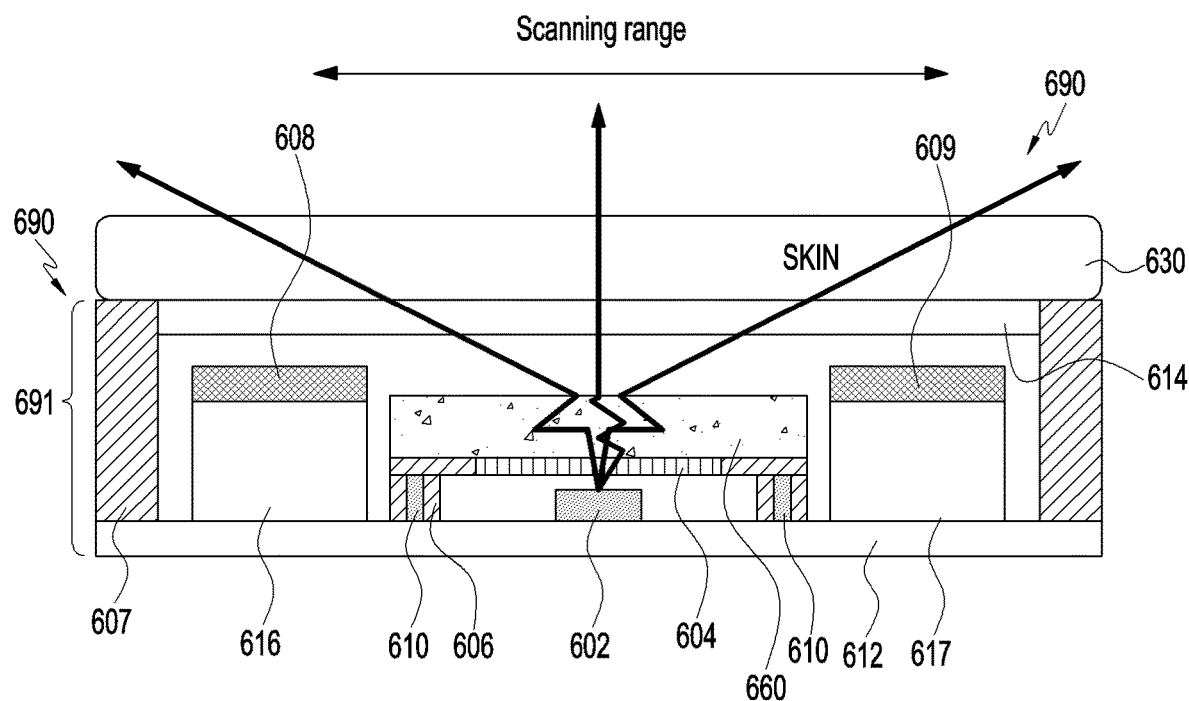
FIG. 6B is a cross-sectional view of a sensor structure of an electronic device according to various embodiments.

FIG. 6A is a cross-sectional view of a sensor structure of an electronic device according to various embodiments. FIG. 6B is a cross-sectional view of a sensor structure of an electronic device according to various embodiments.

Referring to FIG. 6A, a sensor structure 601 (e.g., the sensor structure 501) of an electronic device 600 (e.g., the electronic device 500) may include: a light-emitting element 602 (e.g., the light-emitting element 502); an SLM 604 (e.g., the SLM 504); a first partition wall 606 (e.g., the first partition wall 506); a second partition wall 607 (e.g., the second partition wall 507); one or more photodetectors 608 and 609 (e.g., the one or more photodetectors 508 and 509); at least one connection pin 610 (e.g., the at least one connection pin 510); a support structure 612 (e.g., the support structure 512); a transparent plate 614 (e.g., the transparent plate 514); and/or one or more interposers 616 and 617 (e.g., the one or more interposers 516 and 517).

According to one embodiment, the light-emitting element 602 may be disposed on the support structure 612, and the SLM 604 may be disposed between the light-emitting element 602 and a skin 630. The SLM 604 may be connected to the support structure 612 through the connection pin 610. The connection pin 610 may be coupled to the first partition wall 606 disposed on the support structure 612, and may be formed to support the SLM 604. The transparent plate 614, configured to come into contact with a user's skin 630, may be supported by the second partition wall 607, and a space having a designated height may be formed between the transparent plate 614 and the SLM 604. The photodetector 608 may be disposed near the light-emitting element 602. The one or more photodetectors 608 and 609 may be disposed between the first partition wall 606 and the second partition wall 607, and a space having a designated height may be formed between the transparent plate 614 and the one or more photodetectors 608 and 609. The one or more interposers 616 and 617 may be disposed between the first partition wall 606 and the second partition wall 607 on the top of the support structure 612, and the one or more photodetectors 608 and 609 may be disposed on the tops of the one or more interposers 616 and 617, respectively.

According to one embodiment, considering a feature wherein a blood vessel inside a person's skin changes significantly depending on a heartbeat, the electronic device 600 may identify the position of the blood vessel by measuring a PPG signal. For example, the electronic device 600 may perform control such that the light-emitting element 602 outputs light, and the one or more photodetectors 608 and 609 may sense the light and may detect a PPG signal. For example, the electronic device 600 may identify the position of a blood vessel by using the magnitude of an AC component of the PPG signal (or the SNR of the PPG signal). For example, the electronic device 600 may control the one or more photodetectors 608 and 609 to perform light scanning based on an SLM pattern of the SLM 604. The one or more photodetectors 608 and 609 may determine the position of the blood vessel by identifying the width of the AC component of the PPG signal during the light scanning and selecting the direction having the largest SNR. The SLM may have a two-dimensional array form in which the amplitude and/or phase of light output from the light-emitting element can be modulated when an electrical signal is applied. The SLM pattern is a pattern for allowing light output from the light-emitting element 602 to reach a blood vessel in which a PPG signal is to be measured, and may be called an optimal SLM pattern. The SLM pattern may be a pattern generated under the control of the electronic device 600, a pattern stored in the electronic device 600, or a pattern obtained by partially altering an SLM pattern generated under the control of the electronic device 600 or stored therein.

For example, when state information of a blood vessel is not stored in the electronic device 600, the electronic device 600 may perform a random search for an optimal SLM pattern of the SLM 604. The random search may require a maximum time of about 53 sec (24FPS, 5M Pixel SLM, 100×100 pixels per LED, Amplitude 4 steps, Phase 16 steps, random search). For example, when the state information of a blood vessel is not stored in the electronic device 600, the electronic device 600 may identify information including the scattering state and/or blood distribution state of the skin through a first calibration process and thereafter may calculate the scan angle of light by using the information. Thus, it is possible to reduce the actual search time required to search for an optimal SML pattern of the SLM 604.

For example, when the electronic device 600 stores shape information of a blood vessel in which a PPG signal is to be measured, the electronic device 600 may generate an SLM pattern based on the shape information of the blood vessel. The electronic device 600 may change a direction or the like of the generated SLM pattern so as to search for an optimal SLM pattern of the SLM 604. For example, when the electronic device 600 changes only the direction, a minimum time of about 40 ms (X 10 scan, Y 10 scan, Z 5 scan) may be required.

For example, when the electronic device 600 stores a designated SLM pattern of the SLM 604, the electronic device 600 may change the direction or the like of the designated SLM pattern so as to search for an optimal SLM pattern of the SLM.

Referring to FIG. 6B, as illustrated in FIG. 6A, a sensor structure 691 (e.g., the sensor structure 290) of an electronic device 690 (e.g., the electronic device 500) may include: a light-emitting element 602 (e.g., the light-emitting element 502); an SLM 604 (e.g., the SLM 504); a first partition wall 606 (e.g., the first partition wall 506); a second partition wall 607 (e.g., the second partition wall 507); one or more photodetectors 608 and 609 (e.g., the one or more photodetectors 508 and 509); at least one connection pin 610 (e.g., the at least one connection pin 510); a support structure 612 (e.g., the support structure 512); a transparent plate 614 (e.g., the transparent plate 514); and/or one or more interposers 616 and 617 (e.g., the one or more interposers 516 and 517). The sensor structure 691 may include a scattering medium 660 (a medium, the scattering matrix of which is known; a silicon nano post array) added to the structure of FIG. 6A. The scattering medium 660 may be disposed on the top of the SLM 604, and may be positioned between the SLM 604 and the transparent plate 614. For example, the scattering medium 660 may be disposed between the SLM 604 and the transparent plate 614 such that, when the direction of light output from the light-emitting element 602 is to be changed so as to allow the light to reach a designated blood vessel, the scattering medium 660 is positioned between the SLM 604 and the skin 630 if the direction of the light is greater than the maximum angle of light that can be generated by the SLM 604 (if the direction of the light is greater than the maximum angle of the light that can be generated by the pixel size of the SLM 604). When the scattering medium 660 is disposed between the SLM 604 and the transparent plate 614, the maximum angle of light that can be generated by the SLM 604 may increase. For example, when the highly scattering medium (e.g., a silicon nano post array) 660 is disposed between the SLM 604 and the transparent plate 614, light traveling at a highly oblique angle may also be transferred to the skin through the scattering medium 660. For example, when the electronic device 690 performs phase conjugation of a component of light described above through a SLM pattern, the light may be time-reversed and may be emitted at an oblique angle, and thus the lateral scanning range of the light can be increased. For example, as illustrated in FIG. 6B, the electronic device 690, which includes the sensor structure 691 including the scattering medium 660 disposed between the SLM 604 and the transparent plate 614, may have a wider scanning range than the electronic device 600 of FIG. 6A, which includes the sensor structure 601 that does not include the scattering medium 660.

In the above-described embodiments of FIGS. 6A and 6B, a description has been made of an example in which one light-emitting element 602 is provided. However, according to another embodiment, multiple light-emitting elements 602 may be provided. For example, one SLM 604 may be disposed above multiple light-emitting elements 602 so as to cover the multiple light-emitting elements 602, and the multiple light-emitting elements 602 may be disposed to be surrounded by the partition wall 606.

Figure 7A:
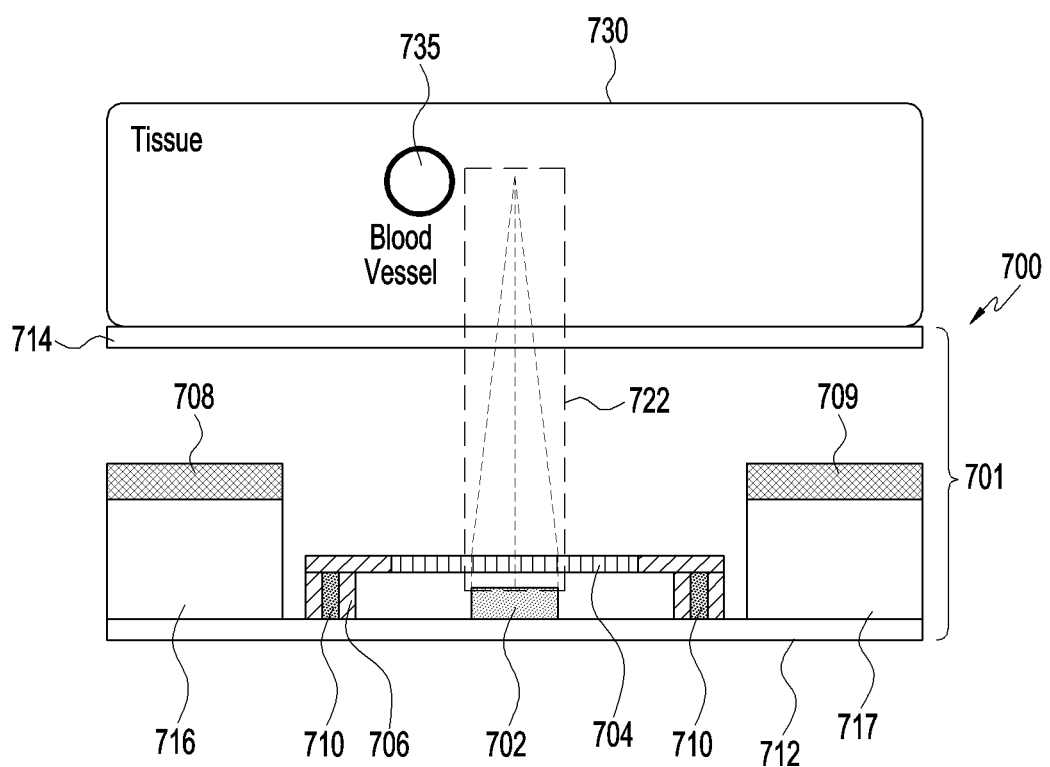
FIG. 7A is a view for describing an operation of focusing light on the position of a blood vessel by using an SLM of an electronic device according to various embodiments.
Figure 7A:
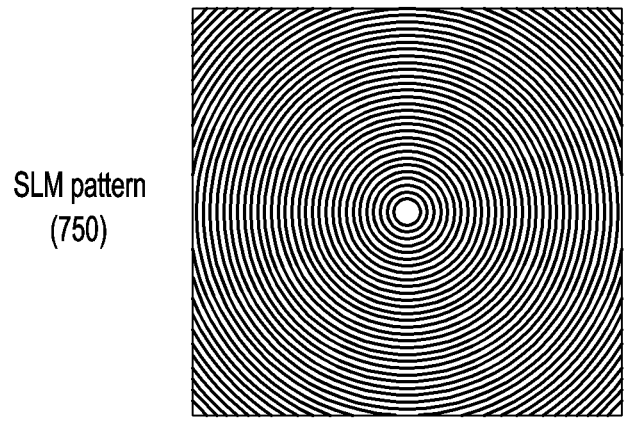
Figure 7A:
Figure 7B:
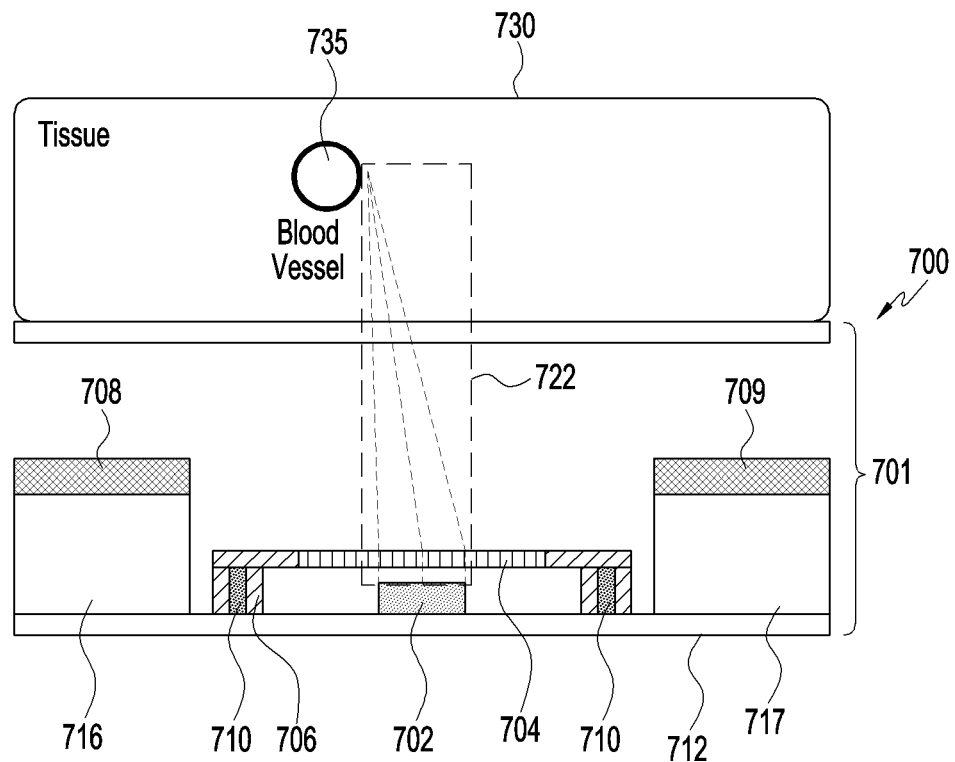
FIG. 7B is a view for describing an operation of focusing light on the position of a blood vessel by using an SLM of an electronic device according to various embodiments.
Figure 7B:
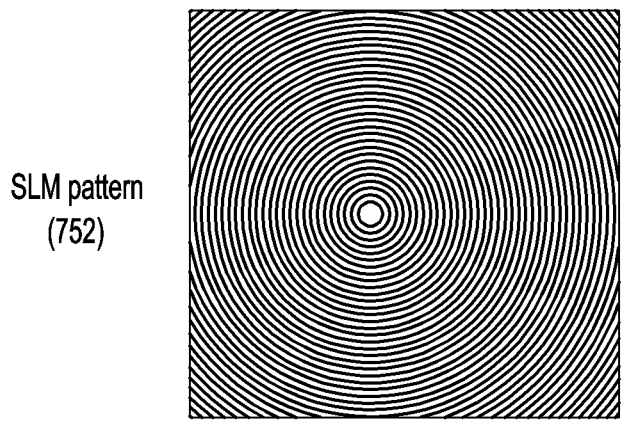
Figure 7B:
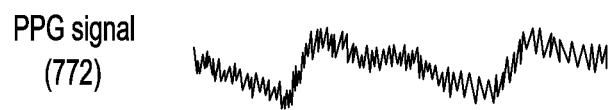
Figure 7C:
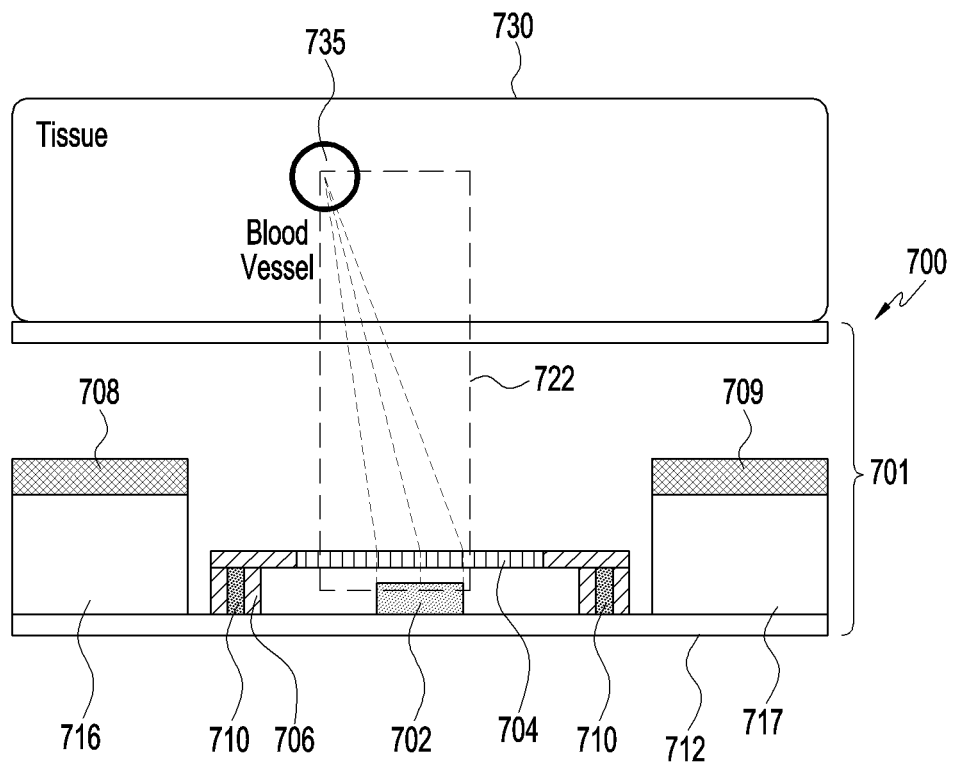
FIG. 7C is a view for describing an operation of focusing light on the position of a blood vessel by using an SLM of an electronic device according to various embodiments.
Figure 7C:
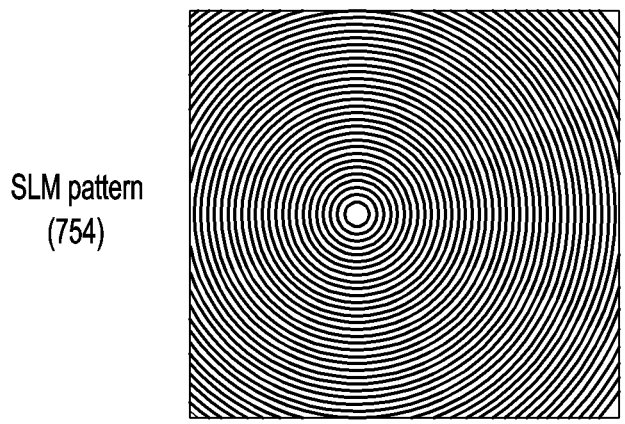
Figure 7C:
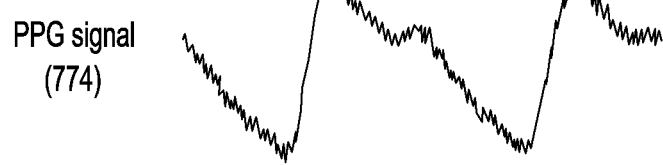

FIG. 7A is a view for describing an operation of focusing light on the position of a blood vessel by using an SLM of an electronic device according to various embodiments. FIG. 7B is a view for describing an operation of focusing light on the position of a blood vessel by using an SLM of an electronic device according to various embodiments. FIG. 7C is a view for describing an operation of focusing light on the position of a blood vessel by using an SLM of an electronic device according to various embodiments.

Referring to FIGS. 7A to 7C, a sensor structure 701 (e.g., the sensor structure 501) of an electronic device 700 (e.g., the electronic device 500) may include: a light-emitting element 702 (e.g., the light-emitting element 502); an SLM 704 (e.g., the SLM 504); first partition wall 706 (e.g., the first partition wall 506); one or more photodetectors 708 and 709 (e.g., the one or more photodetectors 508 and 509); at least one connection pin 710 (e.g., e.g., the at least one connection pin 510); a support structure 712 (e.g., the support structure 512); a transparent plate 714 (e.g., the transparent plate 514); and/or one or more interposers 716 and 717 (e.g., the one or more interposers 516 and 517).

According to one embodiment, the light-emitting element 702 may be disposed on the support structure 712, and the SLM 704 may be disposed between the light-emitting element 702 and a skin 730. The SLM 704 may be connected to the support structure 712 through the connection pin 710. The connection pin 710 may be coupled to the first partition wall 706 disposed on the support structure 712, and may be formed to support the SLM 704. A space having a designated height may be formed between the SLM 704 and the transparent plate 714, which is configured to come into contact with the skin 730 of the user. The one or more photodetectors 708 and 709 may be disposed near the light-emitting element 702. The one or more photodetectors 708 may be disposed outside the first partition wall 706, and a space having a designated height may be formed between the transparent plate 714 and the one or more photodetectors 708. The one or more interposers 716 and 717 may be disposed outside the first partition wall 706 on the top of the support structure 712, and the one or more photodetectors 708 and 709 may be disposed on the tops of the one or more interposers 716 and 717, respectively.

According to one embodiment, as illustrated in FIG. 7A, the electronic device 700 may cause the SLM 704 to output an SLM pattern 750 through which light 722 is focused on a position corresponding to the light-emitting element 702. Since the light 722 in FIG. 7A has been focused onto a portion having no blood vessel 735 in which a PPG signal is to be measured, a PPG signal generated by the blood vessel 735 may not be sensed, and a PPG signal waveform 770 as illustrated in FIG. 7A may be detected.

According to one embodiment, the electronic device 700 may output an SLM pattern 752 of FIG. 7B, which is obtained by shifting the SLM pattern 750 of FIG. 7A to the left, in order to move the focal position of the light 722 to the left, and the position on which the light 722 is focused may also change according to the SLM pattern 752 changed as illustrated in FIG. 7B. In the SLM pattern 752 in FIG. 7B, only the position of the SLM pattern 750 of FIG. 7A has been shifted to the left while the shape of the SLM pattern 750 is maintained. Thus, the SLM pattern 752 may be a pattern in which the focal length of light is maintained and in which only the position on which the light is focused has been moved. According to the above-described operation in FIG. 7B, some PPG signals generated by the blood vessel 735 may be sensed, and thus, as illustrated in FIG. 7B, a PPG signal waveform 772 that is more precise than the PPG signal waveform 770 in FIG. 7A may be detected.

According to one embodiment, the electronic device 700 may output an SLM pattern 754 of FIG. 7C, which is obtained by shifting the SLM pattern 752 of FIG. 7B to the left, in order to move the focal position of the light focused as illustrated in FIG. 7B to the left. The position on which the light 722 is focused may also change according to the SLM pattern 754, which is changed as illustrated in FIG. 7C, and thus the light 722 may be focused on the position of the blood vessel 735. According to the above-described operation in FIG. 7C, most PPG signals generated by the blood vessel 735 may be sensed, and thus, as illustrated in FIG. 7C, a PPG signal waveform 774 that is more precise than the PPG signal waveform 772 in FIG. 7B may be detected.

In the above-described embodiments of FIGS. 7A to 7C, a description has been made only of the case in which the light 722 is laterally scanned. However, the electronic device 700 may perform a light-scanning operation in a depth direction (also called an axial direction) with different focal lengths by changing the line widths of an SLM pattern and the space between the line widths.

In the above-described embodiments of FIGS. 7A to 7C, a description has been made of an example in which the SLM patterns are Fresnel patterns. However, according to another embodiment, the SLM patterns may be grating patterns or patterns formed to correspond to other types of blood vessel distribution.

In each of the above-described embodiments of FIGS. 7A to 7C, a description has been made of an example in which an SLM pattern is shifted in order to move the focal position of light. However, according to another embodiment, the focal position may also be moved by additionally applying a phase gradient in the direction in which the focal position is desired to be moved while the shape of a pattern is maintained.

In the above-described embodiments of FIGS. 7A to 7C, a description has been made of examples in which one light-emitting element 702 is provided. However, according to another embodiment, multiple light-emitting elements 702 may be provided. For example, one SLM 704 may be disposed above multiple light-emitting elements 702 so as to cover the multiple light-emitting elements 702, and the multiple light-emitting elements 702 may be disposed in the state of being surrounded by the partition wall 706.

Figure 8A:
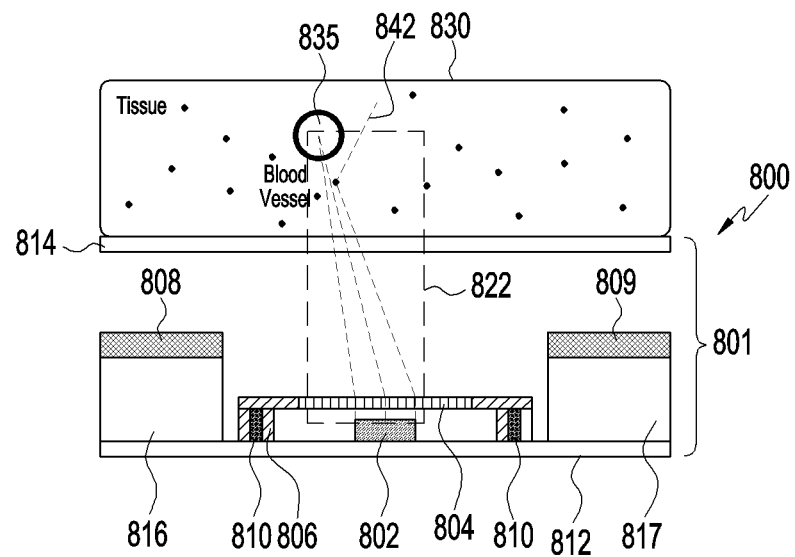
FIG. 8A is a view for describing an operation for reducing the noise of a PPG signal of an electronic device according to various embodiments.
Figure 8B:
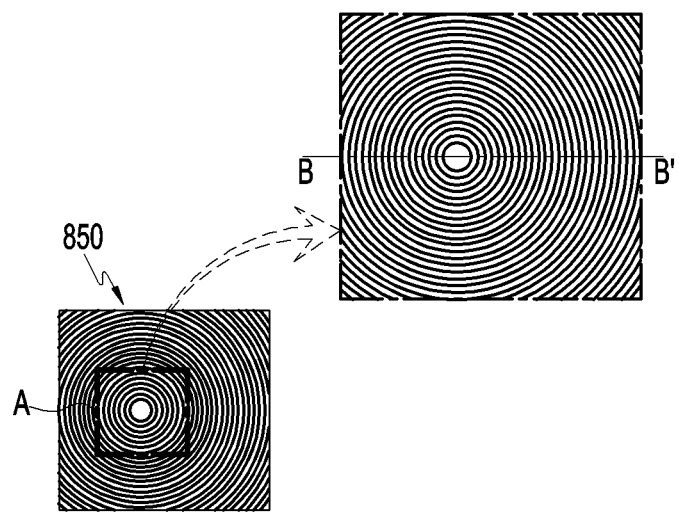
FIG. 8B is a view for describing an operation for reducing the noise of a PPG signal of an electronic device according to various embodiments.
Figure 8C:
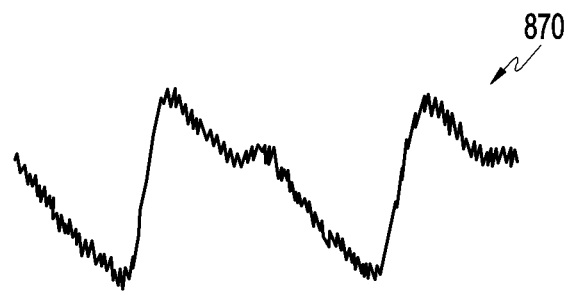
FIG. 8C is a view for describing an operation for reducing the noise of a PPG signal of an electronic device according to various embodiments.
Figure 8D:
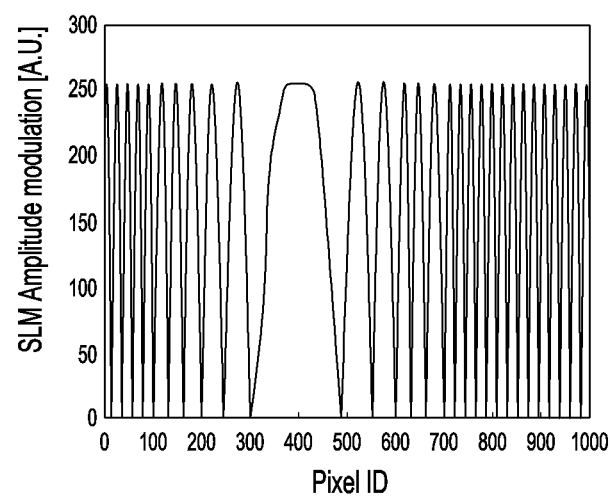
FIG. 8D is a view for describing an operation for reducing the noise of a PPG signal of an electronic device according to various embodiments.
Figure 8E:
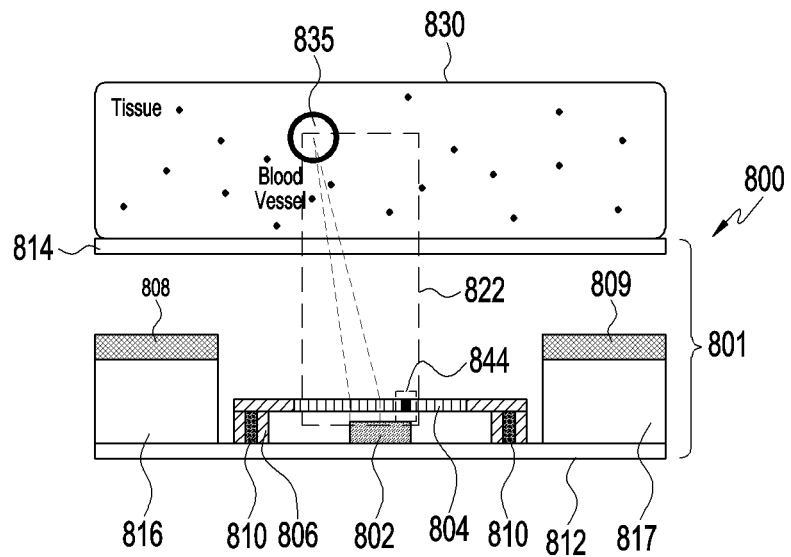
FIG. 8E is a view for describing an operation for reducing the noise of a PPG signal of an electronic device according to various embodiments.
Figure 8F:
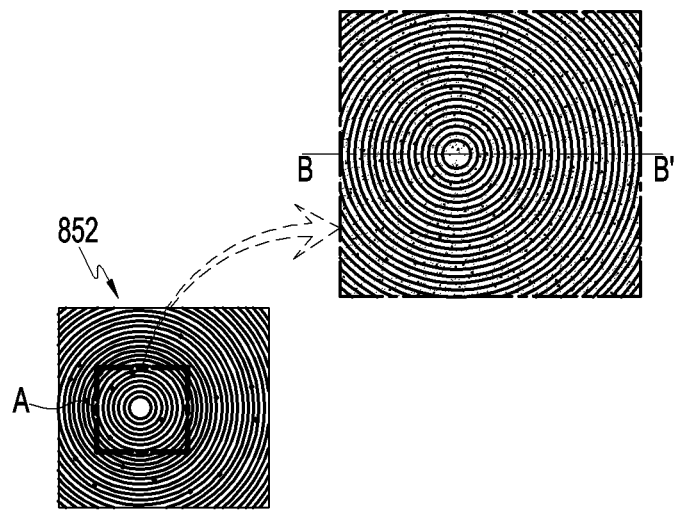
FIG. 8F is a view for describing an operation for reducing the noise of a PPG signal of an electronic device according to various embodiments.
Figure 8G:
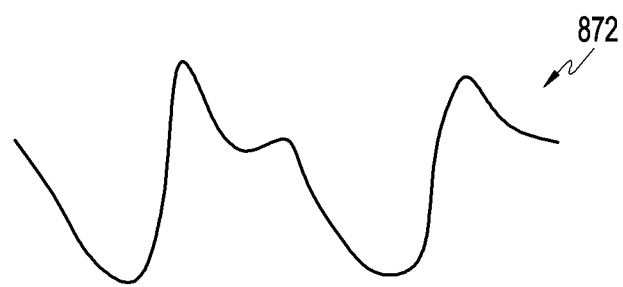
FIG. 8G is a view for describing an operation for reducing the noise of a PPG signal of an electronic device according to various embodiments.
Figure 8H:
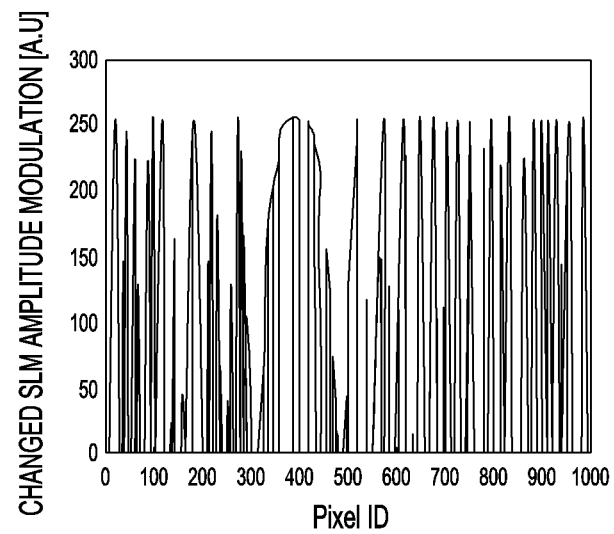
FIG. 8H is a view for describing an operation for reducing the noise of a PPG signal of an electronic device according to various embodiments.
Figure 8I:
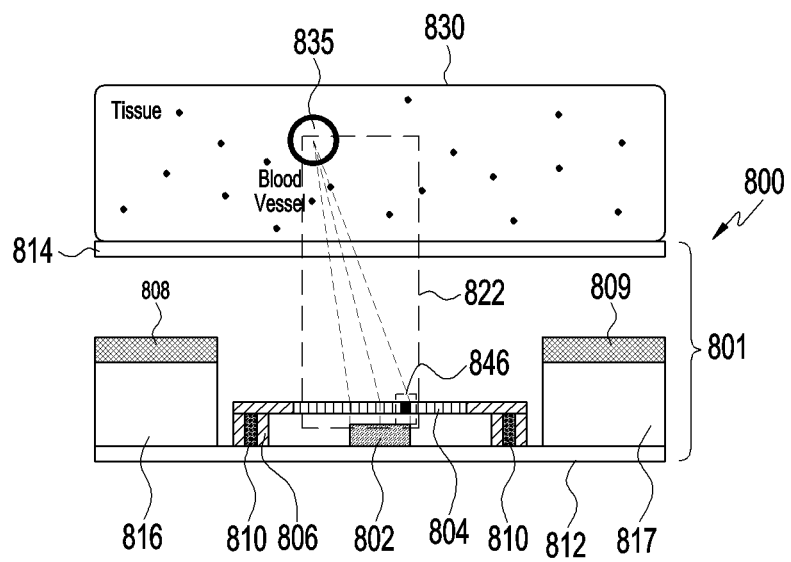
FIG. 8I is a view for describing an operation for reducing the noise of a PPG signal of an electronic device according to various embodiments.
Figure 8J:
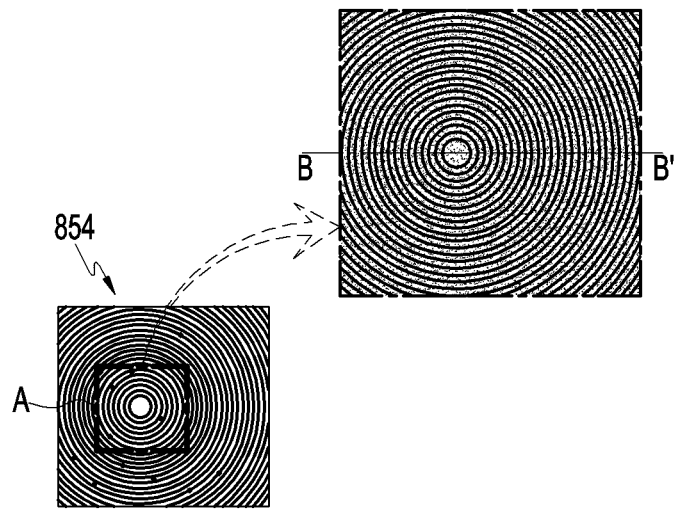
FIG. 8J is a view for describing an operation for reducing the noise of a PPG signal of an electronic device according to various embodiments.
Figure 8K:
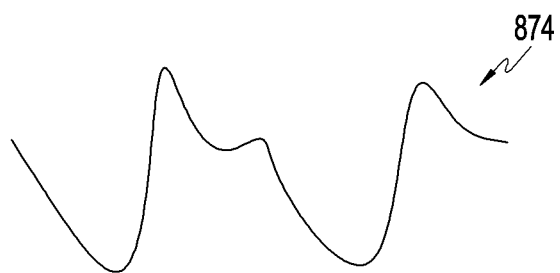
FIG. 8K is a view for describing an operation for reducing the noise of a PPG signal of an electronic device according to various embodiments.
Figure 8L:
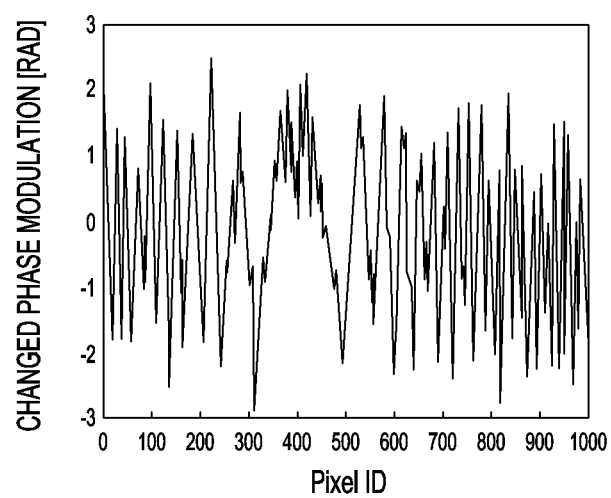
FIG. 8L is a view for describing an operation for reducing the noise of a PPG signal of an electronic device according to various embodiments.
Figure 8M:
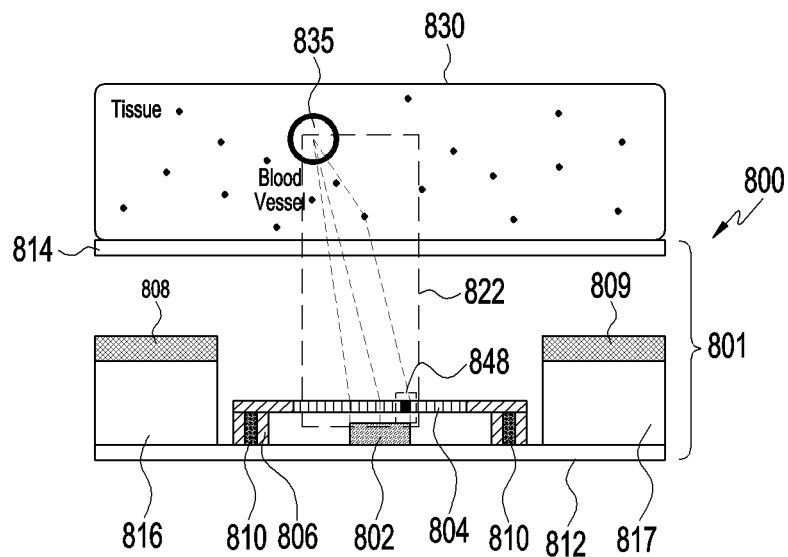
FIG. 8M is a view for describing an operation for reducing the noise of a PPG signal of an electronic device according to various embodiments.
Figure 8N:
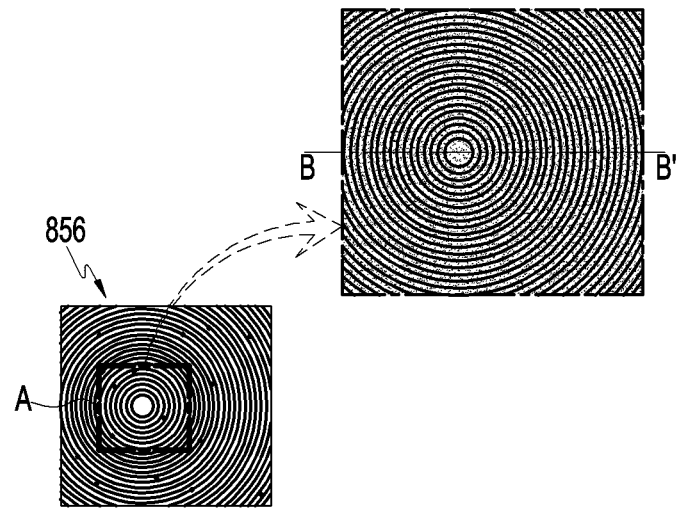
FIG. 8N is a view for describing an operation for reducing the noise of a PPG signal of an electronic device according to various embodiments.
Figure 8O:
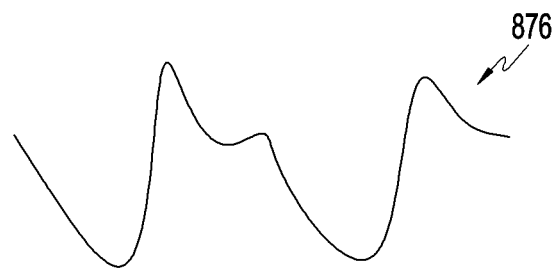
FIG. 8O is a view for describing an operation for reducing the noise of a PPG signal of an electronic device according to various embodiments.
Figure 8P:
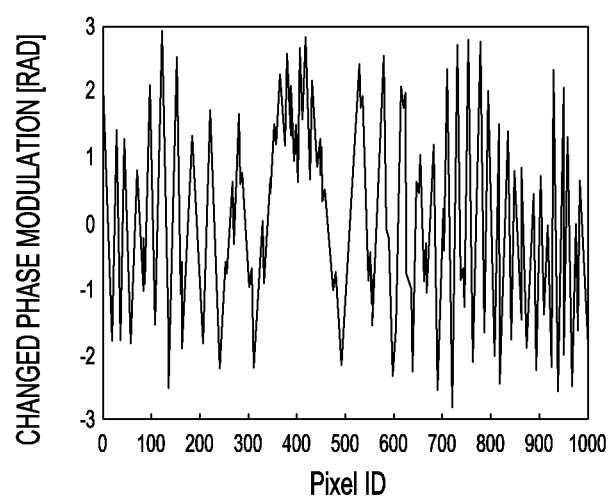
FIG. 8P is a view for describing an operation for reducing the noise of a PPG signal of an electronic device according to various embodiments.

FIG. 8A is a view for describing an operation for reducing the noise of a PPG signal of an electronic device according to various embodiments. FIG. 8B is a view for describing an operation for reducing the noise of a PPG signal of an electronic device according to various embodiments. FIG. 8C is a view for describing an operation for reducing the noise of a PPG signal of an electronic device according to various embodiments. FIG. 8D is a view for describing an operation for reducing the noise of a PPG signal of an electronic device according to various embodiments. FIG. 8E is a view for describing an operation for reducing the noise of a PPG signal of an electronic device according to various embodiments. FIG. 8F is a view for describing an operation for reducing the noise of a PPG signal of an electronic device according to various embodiments. FIG. 8G is a view for describing an operation for reducing the noise of a PPG signal of an electronic device according to various embodiments. FIG. 8H is a view for describing an operation for reducing the noise of a PPG signal of an electronic device according to various embodiments. FIG. 8I is a view for describing an operation for reducing the noise of a PPG signal of an electronic device according to various embodiments. FIG. 8J is a view for describing an operation for reducing the noise of a PPG signal of an electronic device according to various embodiments. FIG. 8K is a view for describing an operation for reducing the noise of a PPG signal of an electronic device according to various embodiments. FIG. 8L is a view for describing an operation for reducing the noise of a PPG signal of an electronic device according to various embodiments. FIG. 8M is a view for describing an operation for reducing the noise of a PPG signal of an electronic device according to various embodiments. FIG. 8N is a view for describing an operation for reducing the noise of a PPG signal of an electronic device according to various embodiments. FIG. 8O is a view for describing an operation for reducing the noise of a PPG signal of an electronic device according to various embodiments. FIG. 8P is a view for describing an operation for reducing the noise of a PPG signal of an electronic device according to various embodiments.

Referring to FIGS. 8A, 8E, 8I, and 8M, a sensor structure 801 (e.g., the sensor structure 501) of an electronic device 800 (e.g., the electronic device 201 or the electronic device 500) may include: a light-emitting element 802 (e.g., the light-emitting element 502); an SLM 804 (e.g., the SLM 504); a first partition wall 806 (e.g., the first partition wall 506); one or more photodetectors 808 and 809 (e.g., the one or more photodetectors 508 and 509); at least one connection pin 810 (e.g., e.g., the at least one connection pin 510); a support structure 812 (e.g., the support structure 512); a transparent plate 814 (e.g., the transparent plate 514); and/or one or more interposers 816 and 817 (e.g., the one or more interposers 516 and 517).

According to one embodiment, the light-emitting element 802 may be disposed on the support structure 812, and the SLM 804 may be disposed between the light-emitting element 802 and a skin 830. The SLM 804 may be connected to the support structure 812 through the connection pin 810. The connection pin 810 may be coupled to the first partition wall 806 disposed on the support structure 812, and may be formed to support the SLM 804. A space having a designated height may be formed between the SLM 804 and the transparent plate 814, which is capable of coming into contact with the skin 830 of a user. The one or more photodetectors 808 and 809 may be disposed near the light-emitting element 802. The one or more photodetectors 808 and 809 may be disposed outside the first partition wall 806, and a space having a designated height may be formed between the transparent plate 814 and the one or more photodetectors 808 and 809. The one or more interposers 816 and 817 may be disposed outside the first partition wall 806 on the top of the support structure 812, and the one or more photodetectors 808 and 809 may be disposed on the tops of one or more interposers 816 and 817, respectively.

Referring to FIGS. 8A to 8P, the electronic device 800 may detect a PPG signal partially including a noise component according to scattering of the skin 830. For example, noise of a PPG signal may be generated according to a characteristic of scattering of light in the skin 830 which may be changed by various components of light, such as the wavelength, traveling direction, phase, and/or polarization of light.

For example, the electronic device 800 may perform control such that the SLM 804 outputs an SLM pattern 850 having the shape illustrated in FIG. 8B, and the SLM pattern 850 illustrated in FIG. 8B may be a pattern for allowing light 822 output from the light-emitting element 802 to be focused on a designated blood vessel 835 (a focal point) at which a PPG signal is to be measured.

For example, the electronic device 800 may perform control such that the light-emitting element 802 outputs the light 822 as illustrated in FIG. 8A while the SLM 804 is controlled to output the SLM pattern 850 of FIG. 8B, and partial light 842 of the output light 822 may travel in another direction without being focused on the blood vessel 835, as illustrated in FIG. 8A, by scattering or the like in the skin 830.

For example, a component of the partial light 842 may not act as a signal in a PPG signal 870, and may be represented by a noise component of the PPG signal 870. The output waveform of the PPG signal 870 may have the shape illustrated in FIG. 8C.

For example, the shape in which light is modulated by the SLM 804 at portion B-B' of part A in the SLM pattern 850 of FIG. 8B may be a Fresnel lens shape, as illustrated in FIG. 8D.

According to one embodiment, the electronic device 800 may use amplitude modulation and/or phase modulation by the SLM 804 in order to reduce the noise of the PPG signal 870.

Referring to FIGS. 8E to 8H, the electronic device 800 may block the light 842 to be scattered, by using amplitude modulation, and may improve the quality of a PPG signal.

According to one embodiment, the electronic device 800 may perform control such that the SLM 804 outputs an SLM pattern 852 having the shape illustrated in FIG. 8F. The SLM pattern 852 illustrated in FIG. 8F may be a pattern for allowing the light 822 output from the light-emitting element 802 to be focused on the designated blood vessel 835 at which a PPG signal is to be measured. Further, the SLM pattern 852 may be a pattern capable of blocking light 844 to be scattered corresponding to the light 842 scattered as illustrated in FIG. 8A.

For example, as illustrated in FIG. 8E, the electronic device 800 may block a component of the light 844 to be scattered by using amplitude modulation to improve the quality of a PPG signal. For example, the electronic device 800 may change the SLM pattern 850 of FIG. 8B to generate (and/or output) the SLM pattern 852 of FIG. 8F. For example, the electronic device 800 may control at least some pixels (e.g. may control a phase and/or an intensity) of the SLM pattern 850 of FIG. 8B in the SLM 804 such that the SLM pattern 852 illustrated in FIG. 8F is output. The at least some pixels may be pixels related to the light 842 to be scattered in FIG. 8E. For example, the electronic device 800 may perform a random search to identify the pixel of the SLM 804 from which the light 842 to be scattered in FIG. 8A is output, and may control the identified pixel such that the SLM pattern 852 illustrated in FIG. 8F is output.

For example, the electronic device 800 may identify the approximate position of a blood vessel, based on the SLM pattern 850 of FIG. 8B, or position information of the blood vessel may be stored in the electronic device 800. Thus, when the electronic device 800 performs the random search, the random search may be performed not for all pixels of the SLM pattern 850 but only for some pixels thereof. For example, a start pixel, at which the random search is started, may be predesignated.

For example, the electronic device 800 may perform control such that the light-emitting element 802 outputs the light 822 as illustrated in FIG. 8E while the SLM 804 outputs the SLM pattern 852 of FIG. 8F. As illustrated in FIG. 8E, the light 842 to be scattered among the light 822 output from the light-emitting element 802 may be prevented from being output out of the SLM 804.

For example, when the electronic device 800 performs control such that the light-emitting element 802 outputs the light 822 as illustrated in FIG. 8A while the SLM 804 outputs the SLM pattern 850 of FIG. 8B, the electronic device 800 may allow at least one pixel of pixels of the SLM 804 to output first light having a first amplitude according to modulation of the light 822. The electronic device 800 may identify a first pixel related to the light 844 to be scattered (a first pixel from which the light 844 to be scattered is output) among the at least one pixel, and may allow the first pixel to output second light having a second amplitude. For example, the electronic device 800 may change the SLM pattern 850 of FIG. 8B to the SLM pattern 852 of FIG. 8F so as to allow the first pixel to output the second light having the second amplitude.

For example, when the light 842 to be scattered is blocked as illustrated in FIG. 8E, the output waveform of a PPG signal 872 may have a shape in which the generation of noise has been reduced, as illustrated in FIG. 8G.

For example, the degree of amplitude modulation by the SLM 804 at portion B-B' of part A in the SLM pattern 852 of FIG. 8F is as illustrated in FIG. 8H.

Referring to FIGS. 8I to 8P, as illustrated in FIGS. 8I and 8M, the electronic device 800 may modulate the phases of components of light 846 and 848 to be scattered so as to prevent the traveling direction of the light 846 and 848 from changing to a direction different from the direction toward the blood vessel 835 even though scattering happens. For example, the electronic device 800 may control at least some pixels of the SLM pattern 850 illustrated in FIG. 8B to modulate the phase of a component of the light 846 of FIG. 8I, and thus may prevent the light 842 from being scattered as illustrated in FIG. 8A and allow the light 846 and 848, which is to be scattered, to travel toward the blood vessel 835 as illustrated FIGS. 8I and 8M. For example, the electronic device 800 may allow the light 846, which is to be scattered, to travel toward the blood vessel 835 as illustrated in FIG. 8I to increase a value of a specific component of a PPG signal, thereby improving a PPG signal quality.

According to one embodiment, the electronic device 800 may perform control such that the SLM 804 outputs an SLM pattern 854 or 856 illustrated in FIG. 8J or 8N. The SLM pattern 854 or 856 illustrated in FIG. 8J or 8N may be a pattern for allowing the light 822 output from the light-emitting element 802 to be focused on the blood vessel 835 in which a PPG signal is to be measured.

According to one embodiment, the electronic device 800 may perform control such that the light-emitting element 802 outputs the light 822 as illustrated in FIG. 8I or 8M while the SLM 804 outputs the SLM pattern 854 or 856 illustrated in FIG. 8J or 8N.

For example, the electronic device 800 may phase-modulate the partial light 842 (e.g., the light to be scattered in FIG. 8I or the light 848 to be scattered in FIG. 8M) of the light 822 output by the light-emitting element 802. For example, the electronic device 800 may perform a random search to identify a pixel that is to be phase-modulated in the SLM pattern 850 of FIG. 8B, and may control the identified pixel such that the SLM pattern 854 or 856 illustrated in FIG. 8J or 8N is output. For example, the electronic device 800 may identify, based on the SLM pattern 850 of FIG. 8B, the approximate position of a blood vessel, or the position of the blood vessel may be stored in the electronic device 800. Thus, when the electronic device 800 performs the random search, the random search may be performed not for all pixels of the SLM pattern 850 but only for some pixels thereof. For example, a start pixel for which the random search is started may be predesignated.

For example, when the electronic device 800 performs control such that the light-emitting element 802 outputs the light 822 as illustrated in FIG. 8A while the SLM 804 outputs the SLM pattern 850 of FIG. 8B, the electronic device 800 may allow at least one pixel, among pixels of the SLM 804, to output first light having a first phase according to modulation of the light 822. The electronic device 800 may identify a first pixel related to the light 846 or 848 to be scattered (a first pixel from which the light 846 to be scattered is output or a first pixel from which the light 848 to be scattered is output) among the at least one pixel, and may allow the first pixel to output second light having a second phase. For example, the electronic device 800 may change the SLM pattern 850 of FIG. 8B to the SLM pattern 854 or 856 of FIG. 8J or 8N so as to allow the first pixel to output the second light having the second phase.

For example, as illustrated in FIG. 8I, the traveling direction of the light 846 may not be changed into a direction different from the direction toward the blood vessel 835 according to phase modulation of the light 846 to be scattered, and thus the output waveform of a PPG signal 874 may have a shape in which the generation of noise has been reduced, as illustrated in FIG. 8K.

For example, as illustrated in FIG. 8M, the traveling direction of the light 848 may be changed according to phase modulation of the light 848 to be scattered so that the light 848 travels toward the blood vessel 835, and thus the output waveform of a PPG signal 876 may have a shape in which the generation of noise has been reduced as illustrated in FIG. 8O.

For example, the phase modulation by the SLM 804 at portion B-B' of part A in the SLM pattern 854 of FIG. 8J is as illustrated in FIG. 8L.

For example, the phase modulation by the SLM 804 at portion B-B' of part A in the SLM pattern 856 of FIG. 8N is as illustrated in FIG. 8P.

The above-mentioned electronic device in FIGS. 5A to 8P has been described as performing an operation of preventing scattering of light and a change in the direction of light to improve signal quality (e.g., PPG signal quality). According to one embodiment, in order to improve a PPG signal quality, the distance between an SLM and a transparent plate of a sensor structure of the electronic device may be important. For example, in order to improve the PPG signal quality, securing a maximum light-scanning range may be important, and in order to secure the maximum light-scanning range, the distance between an SLM and a transparent plate of a sensor structure of the electronic device may be important. For example, in order for the electronic device to secure the maximum light-scanning range, the SLM and the transparent plate are required to be far from each other, and thus adjusting the distance between the SLM and the transparent plate may be important.

The SLM patterns output by the SLM in order to improve PPG signal quality in FIGS. 5A to 8P are designed to transmit light from the light-emitting element while maximally preventing the light from being split in different directions, and thus are required to be formed to collimate light from the light-emitting element having a limited size, and may be formed so as not to consider scattering, unlike the above-described embodiments of FIGS. 8A to 8P. For example, for high efficiency of the electronic device, the SLM may not be allowed to simultaneously modulate an amplitude and a phase, or the SLM may allow to perform only amplitude modulation or only phase modulation.

Figure 9:
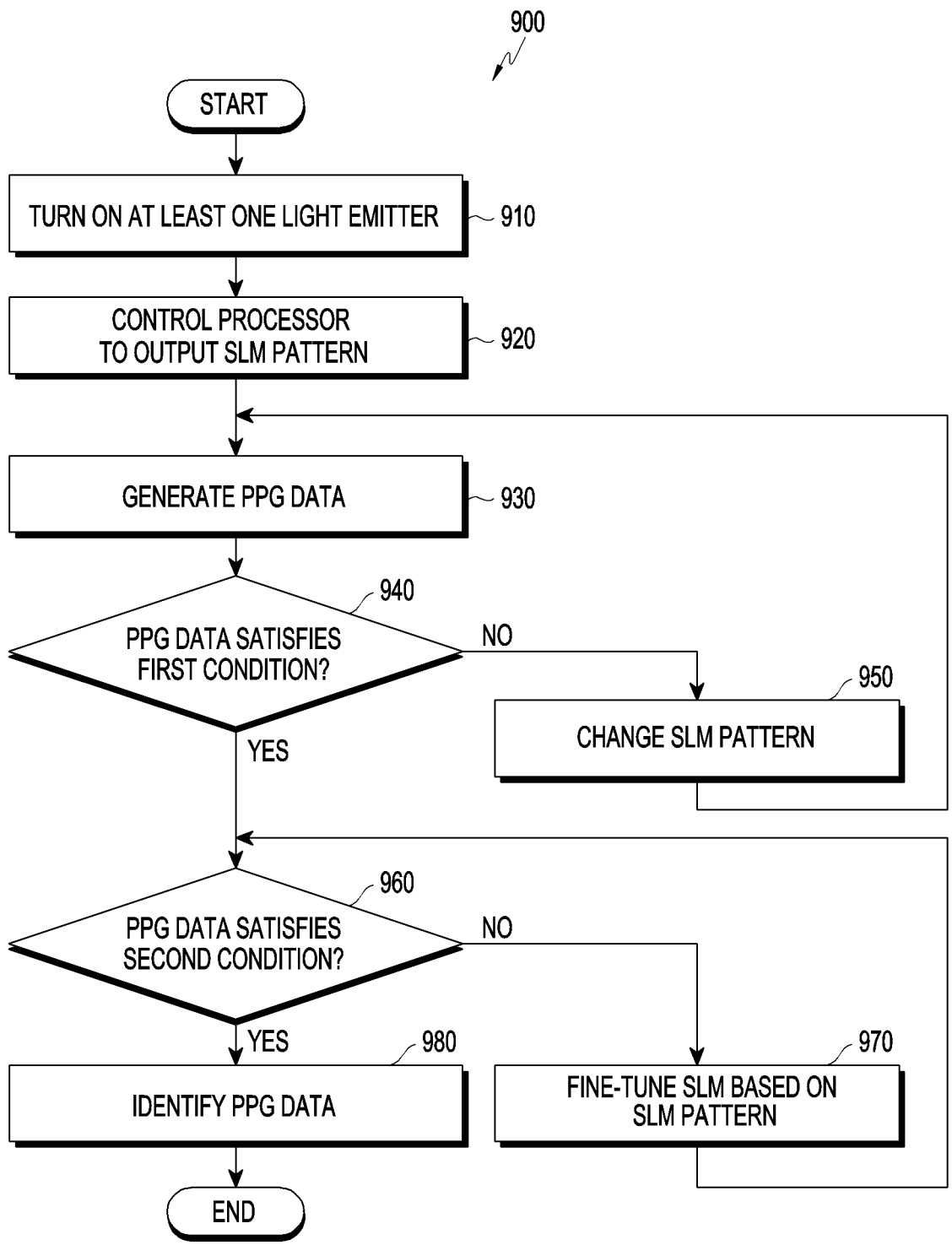
FIG. 9 is a flowchart of operations of an electronic device according to various embodiments.

FIG. 9 is a flowchart 900 of operations of an electronic device (e.g., the electronic device 201, the controller 220 of the electronic device 201, the processing circuit 225 of the electronic device 201, or the electronic device 500) according to various embodiments.

According to one embodiment, the relative position of a user's blood vessel, in which a PPG signal is to be measured from the position of a sensor structure (e.g. the sensor structure 290) of the electronic device, may change depending on the user's motion, the user's style of use of the electronic device, etc.

For example, in the case of a conventional electronic device having a sensor structure attached thereto (e.g. a wearable electronic device), the accuracy of biometric information that can be obtained from a PPG signal acquired using the sensor structure may greatly differ depending on each user' styles of wearing a wearable electronic device (e.g. wearing the electronic device while leaving a small space between the electronic device and the user's skin, wearing the electronic device so as to be in contact with the user's skin, etc.). For example, conventionally, when a user wears a wearable electronic device while leaving a small space between the wearable electronic device and the user's skin, the wearable electronic device is moved even by a small motion of the user, and thus a light-emitting device (e.g., light-emitting device 240) of the sensor structure may not accurately emit light to the radial artery. For example, conventionally, when a user wears a wearable electronic device in close contact with the user's skin, the absorption/reflection waveform of a PPG signal acquired by the sensor structure may be reversed or distorted depending on whether a blood vessel is dilated.

Referring to FIG. 9, in order to solve the problem with the conventional electronic device having a sensor structure attached thereto, for example, the problem in which the relative position of a blood vessel, in which a PPG signal is to be measured, may change, an electronic device capable of measuring a PPG signal may identify the position of a blood vessel, based on an SLM pattern output by an SLM (e.g., the SLM 504). When the electronic device identifies the position of the blood vessel, the electronic device may reduce a scattering component that exists until light output from a light-emitting device (e.g., the light-emitting device 240) including at least one light-emitting element (e.g., the light-emitting element 502) reaches a blood vessel in the skin. For example, the electronic device may reduce, based on the SLM pattern that is finally selected for identifying the position of the blood vessel, noise of the PPG signal by using amplitude modulation or phase modulation by the SLM. For example, the electronic device may control at least some pixels based on the selected SLM pattern to generate PPG data (also called a PPG signal) by using a light detection device (e.g., the light detection device 360) including one or more first photodetectors (e.g., the one or more photodetectors 508 and 509).

In operation 910, the electronic device may turn on at least one light-emitting element.

According to one embodiment, the electronic device may turn on at least one light-emitting element such that the light-emitting element outputs light.

In operation 920, the electronic device may perform control such that a processor outputs a designated SLM pattern.

According to one embodiment, the SLM pattern may be a pattern designated so as to allow the light output from the at least one light-emitting element to be focused on a first portion. For example, the SLM pattern may be a Fresnel pattern. In another example, if a blood vessel is linearly distributed, the SLM pattern may be a grating pattern. In another example, in the case of curved-blood-vessel distribution, the SLM pattern may be a pattern formed to correspond to the blood vessel distribution.

According to one embodiment, the electronic device may perform control such that the processor outputs the SLM pattern through an SLM while the at least one light-emitting element outputs the light.

In operation 930, the electronic device may generate PPG data by using one or more photodetectors.

According to one embodiment, the electronic device 701 may sense light by one or more photodetectors to generate PPG data (may measure a PPG signal).

In operation 940, the electronic device may determine whether the PPG data satisfies a first condition.

When the PPG data satisfies the first condition, the electronic device may perform operation 960. Otherwise, the electronic device may perform operation 950.

According to one embodiment, the electronic device may determine whether the size of the PPG data (the magnitude of an AC component of a PPG signal (or the SNR of the PPG signal)) is a maximum measurable value. For example, when the size of the PPG data (the magnitude of an AC component of a PPG signal (or the SNR of the PPG signal)) is the maximum value, the electronic device may perform operation 960. Otherwise, the electronic device may perform operation 950.

According to another embodiment, the electronic device may determine whether the size of the PPG data (the magnitude of an AC component of a PPG signal (or the SNR of the PPG signal)) is equal to or greater than a designated threshold value. For example, when the size of the PPG data (the magnitude of an AC component of a PPG signal (or the SNR of the PPG signal)) is equal to or greater than the designated threshold value, the electronic device may perform operation 960. Otherwise, the electronic device may perform operation 950.

In operation 950, the electronic device may perform control such that the SLM changes the SLM pattern and outputs a changed SLM pattern.

According to one embodiment, the electronic device may change the SLM pattern by shifting the SLM pattern in a first direction (upward, downward, leftward, or rightward) according to a designated criterion or through a random search.

In operation 960, the electronic device may determine whether the PPG data satisfies a second condition.

When the PPG data satisfies the second condition, operation 980 may be performed. Otherwise, operation 970 may be performed.

According to one embodiment, the electronic device may determine whether the SNR of a PPG signal is a maximum measurable value. For example, when the SNR of a PPG signal is the maximum measurable value, operation 970 may be performed. Otherwise, operation 960 may be performed.

In operation 970, the electronic device may fine-tune the SLM based on the SLM pattern.

According to one embodiment, the electronic device may control at least some pixels of the SLM pattern (e.g. control the output intensity of light and/or control the phase of light) so as to change the SLM pattern.

For example, the at least some pixels may be patterns related to light to be scattered. The electronic device may perform a random search to identify a pixel of the SLM from which light to be scattered is output, and may control the identified pixel to change the SLM pattern. For example, when the electronic device performs the random search, the random search may be performed not for all pixels of the SLM pattern but only for some pixels thereof, based on position information of a blood vessel to be measured. For example, a start pixel for which the random search is started may be predesignated.

According to one embodiment, when light passing through the SLM is output in the state of having a modulated amplitude or a modulated phase, the electronic device may control at least one pixel of the SLM such that partial light having a first amplitude or a first phase has an amplitude or a phase that is different from the first amplitude or the first phase.

For example, when the electronic device performs control such that the light-emitting element outputs light while the SLM outputs the SLM pattern, the electronic device may allow at least one pixel of pixels of the SLM to output first light having a first amplitude or a first phase according to light modulation. The electronic device may identify a first pixel related to light to be scattered (a first pixel from which light to be scattered is output) among the at least one pixel, and may change the SLM pattern such that the first pixel outputs second light having a second amplitude or a second phase.

In operation 980, the electronic device may identify the PPG data.

According to one embodiment, the electronic device 701 may sense light by using a photodetector to generate the PPG data (detect a PPG signal).

According to one embodiment, the final SLM pattern determined through operations 910 to 970 may be determined to be an SLM pattern for selecting the position of a blood vessel and minimize skin scattering, and thus the PPG signal measured through operation 980 may be a PPG signal having an improved signal quality.

According to various embodiments, a method for biometric information detection using a spatial light modulator (SLM) (e.g., the SLM 504) of an electronic device (e.g., the electronic device 500) may include: turning on at least one light-emitting element (e.g., the light-emitting element 502) of the electronic device; controlling at least one pixel of the SLM such that the SLM of the electronic device outputs a first pattern by using light output from the light-emitting element; and generating photoplethysmogram (PPG) data by using a light-receiving element (e.g. the photodetector 508) of the electronic device.

According to various embodiments, the method may further include: performing control, based on the first pattern, such that at least one pixel of pixels of the SLM outputs first light having a first amplitude or a first phase; identifying a first pixel related to light to be scattered among the at least one pixel; and performing control such that the first pixel outputs second light having a second amplitude or a second phase.

According to various embodiments, the method may further include: controlling at least one pixel of the SLM such that the SLM outputs a pattern obtained by shifting the first pattern; and generating new PPG data by using a photodiode while the SLM outputs the shifted pattern.

According to various embodiments, the method may include: controlling, based on the magnitude of an AC component of a PPG signal wave included in the PPG data, the at least one pixel of the SLM such that the SLM outputs the pattern obtained by shifting the first pattern, and generating the new PPG data.

Figure 10A:
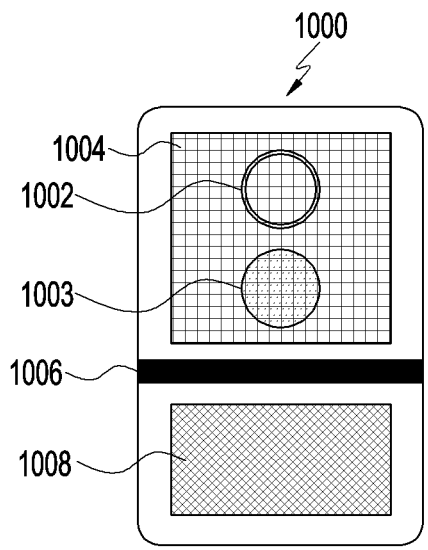
FIG. 10A is a plan view illustrating main elements of an electronic device according to various embodiments.
Figure 10B:
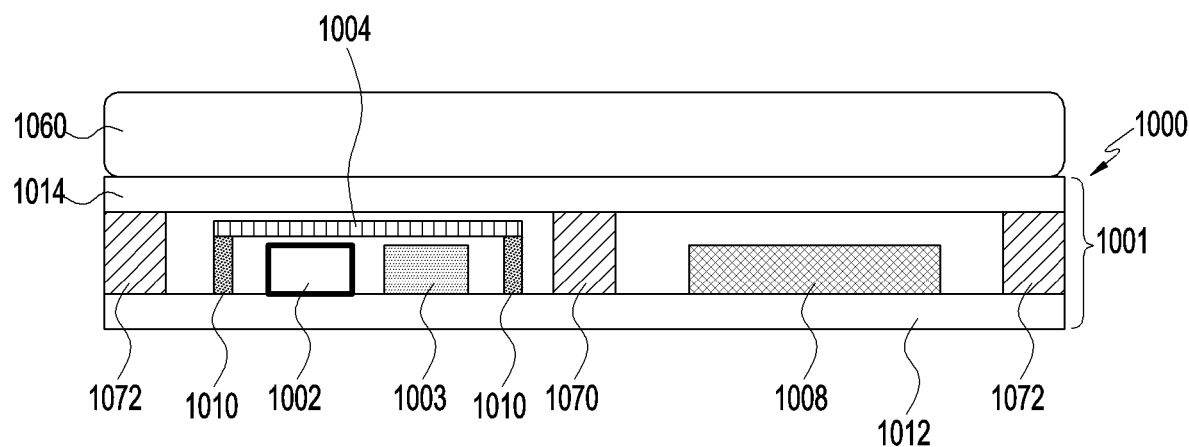
FIG. 10B is a cross-sectional view of an electronic device according to various embodiments.

FIG. 10A is a plan view illustrating main elements of an electronic device according to various embodiments. FIG. 10B is a cross-sectional view of an electronic device according to various embodiments. FIG. 10C is a cross-sectional view of an electronic device according to various embodiments. FIG. 10D illustrates an example of an SLM waveform according to various embodiments. FIG. 10E illustrates an example of an SLM waveform according to various embodiments.

Referring to FIGS. 10B to 10D, a sensor structure 1001 (e.g., the sensor structure 290) of an electronic device 1000 (e.g., the electronic device 201) may include: a first light-emitting element 1002 (e.g., the first light-emitting element 242); a second light-emitting element 1003 (e.g., second light-emitting element 244); an SLM 1004 (e.g., the SLM 280); a photodetector 1008 (e.g., the first photodetector 262); a first partition wall 1070, a second partition wall 1072; a support structure 1012; a transparent plate 1014; and a connection pin 1010.

Referring to FIGS. 10B to 10D, the sensor structure 1001 may include the support structure 1012, and the first light-emitting element 1002 (e.g., the first light-emitting element 242, the second light-emitting element 1003 (e.g., second light-emitting element 244), and at least one photodetector 1008 (e.g., the first photodetector 262, the second photodetector 264, and/or the third photodetector 266) may be disposed on the support structure 1012.

The first light-emitting element 1002 and the second light-emitting element 1003 may be disposed between the first partition wall 1070 on the support structure 1012 and the second partition wall 1072 on the support structure 1012, and the at least one photodetector 1008 may be disposed between the first partition wall 1070 and the second partition wall 1072. For example, the support structure 1012 may be electrically connected to the first light-emitting element 1002 and the second light-emitting element 1003. For example, a processing circuit (e.g., the processing circuit 225) of the electronic device 1000 may transfer a control signal to the first light-emitting element 1002 and the second light-emitting element 1003 via a wire. The transparent plate 1014, configured to come into contact with a user's skin 1060, may be disposed on the tops of the first partition wall 1070 and the second partition wall 1072. A space may be formed between the transparent plate 1014 and each of the first light-emitting element 1002, the second light-emitting element 1003, and the at least one photodetector 1008 according to the lengths (heights) of the first partition wall 1070 and the second partition wall 1072. The SLM 1004 may be disposed just above the first light-emitting element 1002 and the second light-emitting element 1003, and may be connected to the support structure 1012 through the connection pin 1010. For example, the connection pin 1010 may be an electrical path for transferring a control signal from the processing circuit (e.g., the processing circuit 225) of the electronic device. A space having a designated height may be formed between the SLM 1004 and each of the first light-emitting element 1002 and the second light-emitting element 1003 according to the height (length) of the connection pin 1010. A space having a designated height may be formed between the SLM 1004 and the transparent plate 1014.

According to one embodiment, the electronic device 1000 uses the SLM 1004 having a 2D array structure capable of modulating the amplitude and/or phase of light by an electrical signal without using a lens as in conventional PPG sensors, and thus may collimate light. For example, the SLM 1004 may have a size large enough to modulate both the first light-emitting element 1002 and the second light-emitting element 1003, and may be positioned above the first light-emitting element 1002 and the second light-emitting element 1003 while leaving a space therebetween. For example, the first light-emitting element 1002 and the second light-emitting element 1003 may be disposed closest to each other within an allowable range.

Referring to FIGS. 10C to 10E, the electronic device 1000 may perform control such that the first light-emitting element 1002 and the second light-emitting element 1003 operate in sequence. For example, the electronic device 1000 may generate (or form) and/or store an SLM pattern corresponding to each of the light-emitting elements. Referring to FIG. 10C, when the electronic device 1000 performs control such that the first light-emitting element 1002 emits light, the electronic device 1000 may perform control such that the SLM 1004 outputs a first SLM pattern corresponding to the first light-emitting element, as illustrated in FIG. 10D. For example, when the electronic device 1000 performs control such that the second light-emitting element 1003 emits light, the electronic device 1000 may perform control such that the SLM 1004 outputs a second SLM pattern corresponding to the second light-emitting element 1003, as illustrated in FIG. 10E.

In the above-described embodiments of FIGS. 10A to 10E, a description has been made of an example in which the electronic device 1000 includes two light-emitting elements, i.e., the first light-emitting element 1002 and the second light-emitting element 1003. However, according to another embodiment, the electronic device including the SLM may include light-emitting elements, the number of which is greater than the number of the light-emitting elements of FIGS. 10A to 10C, and many light-emitting elements may be disposed in a support structure having a narrow area.

According to the above-described embodiments of FIGS. 10A and 10E, each SLM pattern is formed by the SLM 1004 through control of the electronic device 1000 only when the corresponding light-emitting element operates, and thus the size of the SLM pattern may not be limited. For example, the electronic device 1000 may generate a large SLM pattern so as to collimate a broad spectrum of light output from the light-emitting element. For example, the electronic device 1000 may change the position of the SLM pattern by using a pixel size of the SLM, and thus may minimize the influence of misalignment due to process variation.

Figure 11A:
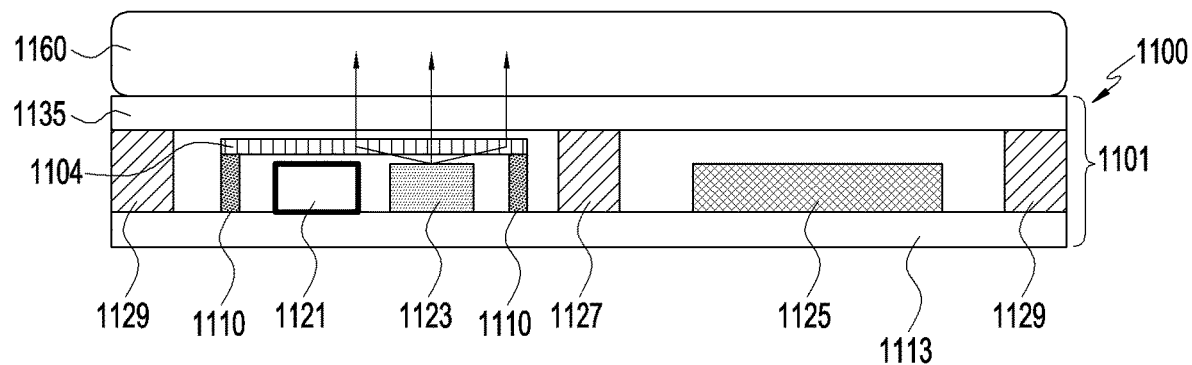
FIG. 11A is a view for describing an electronic device capable of correcting process variation according to various embodiments.
Figure 11B:
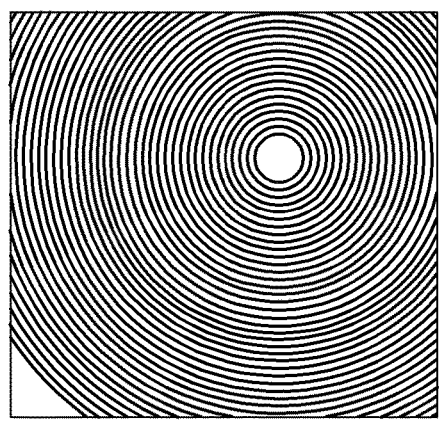
FIG. 11B is a view for describing an electronic device capable of correcting process variation according to various embodiments.
Figure 11C:
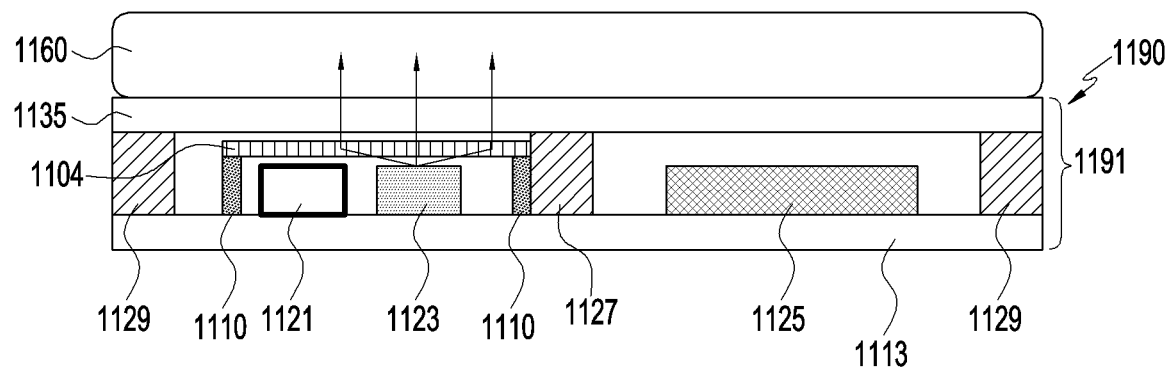
FIG. 11C is a view for describing an electronic device capable of correcting process variation according to various embodiments.
Figure 11D:
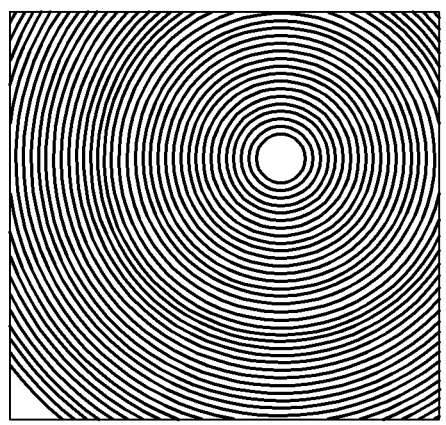
FIG. 11D is a view for describing an electronic device capable of correcting process variation according to various embodiments.

FIG. 11A is a view for describing an electronic device capable of correcting process variation according to various embodiments. FIG. 11B is a view for describing an electronic device capable of correcting process variation according to various embodiments. FIG. 11C is a view for describing an electronic device capable of correcting process variation according to various embodiments. FIG. 11D is a view for describing an electronic device capable of correcting process variation according to various embodiments.

Referring to FIG. 11A, a sensor structure 1101 (e.g., the sensor structure 1001) of an electronic device 1100 (e.g., the electronic device 1000) may include: a first light-emitting element 1121 (e.g., first light-emitting element 1002); a second light-emitting element 1123 (e.g., the second light-emitting element 1003); a photodetector 1125 (e.g., the photodetector 1008); a first partition wall 1127 (e.g., the first partition wall 1070); a second partition wall 1129 (e.g., the second partition wall 1072); a support structure 1133 (e.g., the support structure 1012); a transparent plate 1135 (e.g., the transparent plate 1014); an SLM 1104 (e.g., the SLM 1004); and a connection pin 1110 (e.g., the connection pin 1010).

In the case of the electronic device 1100 including the SLM 1104, correctly aligned as illustrated in FIG. 11, when the electronic device 1100 controls the SLM 1104 to output the SLM pattern of FIG. 11B, which is designated to correspond to the second light-emitting element 1123, crosstalk noise through transparent glass 1135 may be reduced due to the linearity of light output from the second light-emitting element 1123.

Referring to FIG. 11C, like the sensor structure 1101 of the electronic device 1100 in FIG. 11A, a sensor structure 1191 (e.g., the sensor structure 1001) of an electronic device 1190 (e.g., the electronic device 1000) may include: a first light-emitting element 1121 (e.g., first light-emitting element 1002); a second light-emitting element 1123 (e.g., the second light-emitting element 1003); a photodetector 1125 (e.g., the photodetector 1008); a first partition wall 1127 (e.g., the first partition wall 1070); a second partition wall 1129 (e.g., the second partition wall 1072); a support structure 1133 (e.g., the support structure 1012); a transparent plate 1135 (e.g., the transparent plate 1014); an SLM 1104 (e.g., the SLM 1004); and a connection pin 1110 (e.g., the connection pin 1010).

In the case of the electronic device 1100 including the misaligned SLM 1104 illustrated in FIG. 11C, the electronic device 1100 may control the SLM 1104 to output the SLM pattern of FIG. 11D, which is obtained by shifting the SLM pattern designated to correspond to the second light-emitting element 1123, and thus crosstalk noise may be reduced due to the linearity of light output from the second light-emitting element 1123.

According to the above-described embodiments of FIGS. 11A to 11D, when the SLM 1104 is misaligned as illustrated FIG. 11C, crosstalk noise may be minimized by outputting the shifted SLM pattern, as in the case of the electronic device 1100 of FIG. 11A including the correctly aligned SLM 1104.

Each of the electronic devices of FIGS. 10A to 11D may reduce crosstalk noise by minimizing the divergence angle of light emitted from a light-emitting element having a limited size, and thus, as the distance between the SLM and the light-emitting element increases, the crosstalk noise may be more effectively reduced. Therefore, adjusting the distance between the SLM and the light-emitting element may be important. On the other hand, the distance between the SLM and the transparent plate may not be important.

Figure 12:
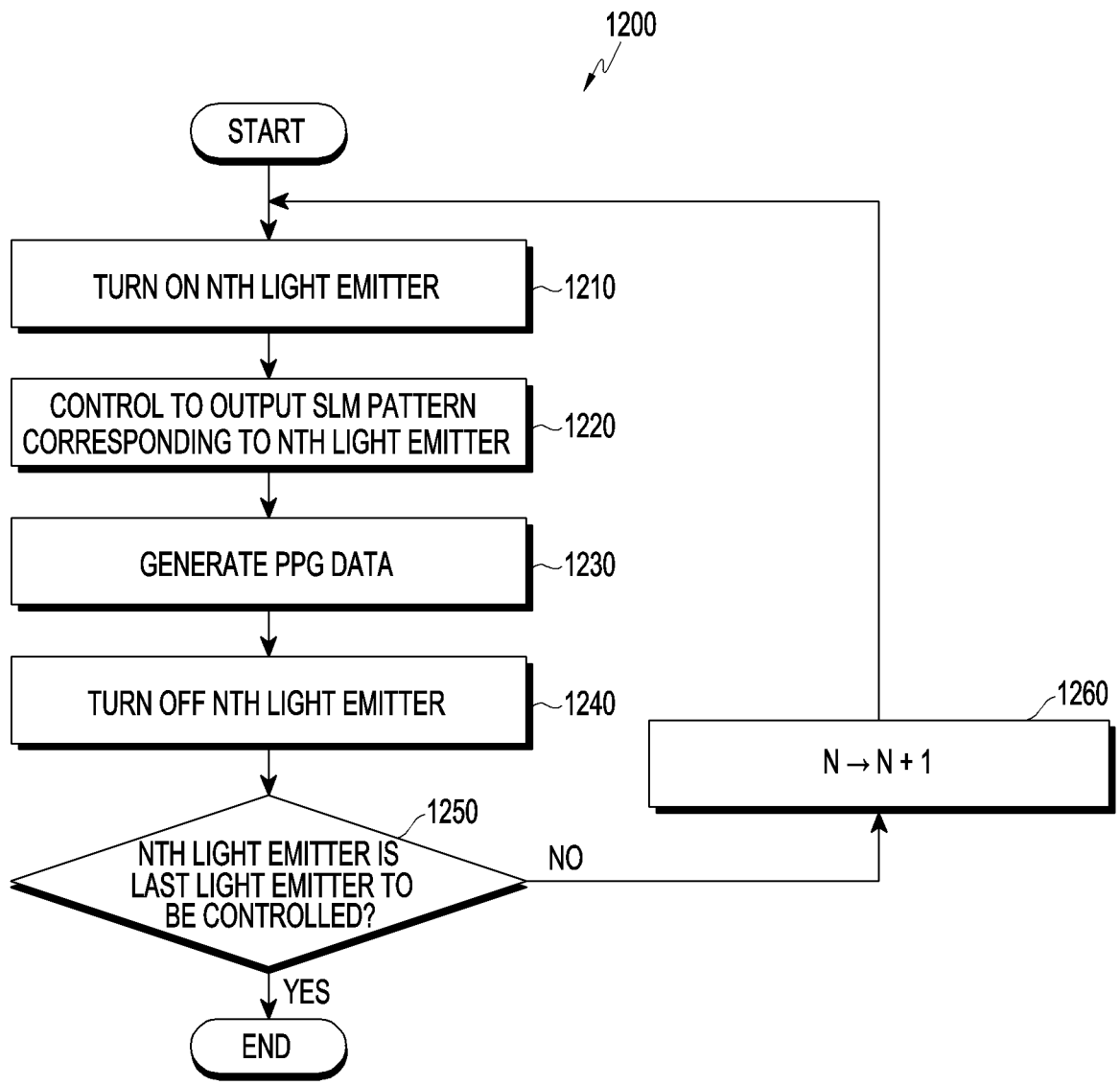
FIG. 12 is a flowchart of operations of an electronic device according to various embodiments.

FIG. 12 is a flowchart 1200 of operations of an electronic device (e.g., the electronic device 201, the controller 220 of the electronic device 201, the processing circuit 225 of the electronic device 201, or the electronic device 1000) according to various embodiments.

Referring to FIG. 12, the electronic device may include N light-emitting elements (e.g., the first light-emitting element 1002 and the second light-emitting element 1003), and the electronic device may control the N light-emitting elements to sequentially operate according to a designated order.

In operation 1210, the electronic device may turn on an Nth light-emitting element.

According to one embodiment, the electronic device may turn on the Nth light-emitting element such that the Nth light-emitting element outputs light.

In operation 1220, the electronic device may control an SLM (e.g., the SLM 1004) to output an SLM pattern corresponding to the Nth light-emitting element.

According to one embodiment, the electronic device may store an SLM pattern corresponding to each of the light-emitting elements.

According to one embodiment, the electronic device may control the SLM to output the SLM pattern corresponding to the Nth light-emitting element while the Nth light-emitting element outputs light.

In operation 1230, the electronic device may generate PPG data.

According to one embodiment, the electronic device may sense light by using at least one photodetector (e.g., the photodetector 1008) to generate the PPG data (measure a PPG signal).

In operation 1240, the electronic device may turn off the Nth light-emitting element.

In operation 1250, the electronic device may determine whether the Nth light-emitting element is the last light-emitting element to be controlled.

When the Nth light-emitting element is the last light-emitting element to be controlled, the operations of the disclosure may be ended. Otherwise, operation 1260 may be performed.

In operation 1260, the electronic device may replace N with N+1.

According to one embodiment, the electronic device may replace N with N+1 so as to control a light-emitting element following the Nth light-emitting element.

Figure 13:
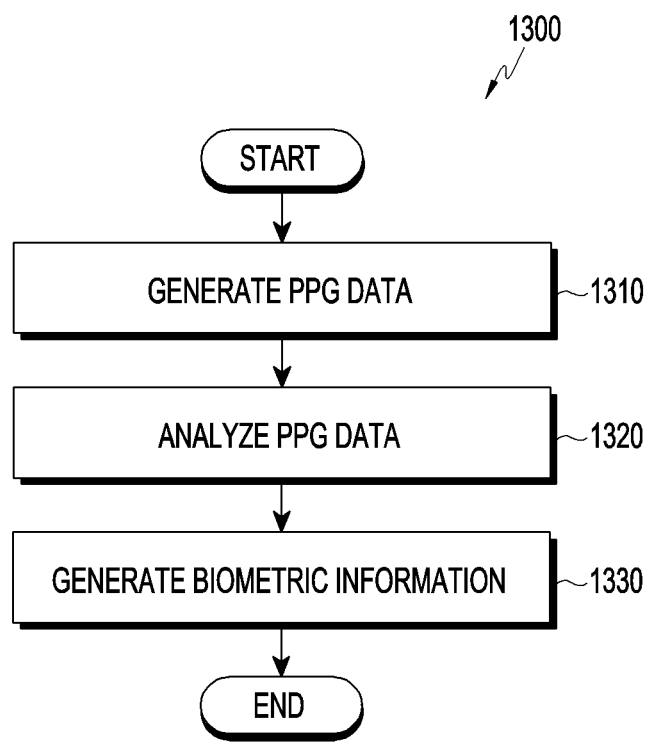
FIG. 13 is a flowchart of operations of an electronic device according to various embodiments.

FIG. 13 is a flowchart of operations of an electronic device (e.g., the electronic device 201, the controller 220 of the electronic device 201, the processing circuit 225 of the electronic device 201, or the electronic device 1000) according to various embodiments.

Referring to FIG. 13, according to the above-described embodiments of FIGS. 2 to 12, the electronic device may detect a PPG signal with improved accuracy compared with a conventional electronic device, and the electronic device may extract various types of biometric information through the PPG signal. For example, in the case of heartbeat information, only the peak of the PPG signal may be extracted and acquired. Biometric information such as blood pressure may be acquired from waveforms (e.g., F1, F2, and F3 waveforms) of the PPG signal having enhanced accuracy.

In operation 1310, the electronic device may generate PPG data.

According to one embodiment, the electronic device may sense light by using at least one photodetector (e.g., the photodetector 1008) to generate the PPG data.

In operation 1320, the electronic device may analyze the PPG data.

According to one embodiment, the electronic device may identify the waveform of a PPG signal, may identify peak information of a PPG signal, may identify frequency information of a PPG signal, and may identify phase information of a PPG signal.

In operation 1330, the electronic device may generate biometric information based on the result of the PPG data analysis.

According to one embodiment, the biometric information may be information about a user's heartbeat, information about blood pressure, a stress index, sleep quality, etc. For example, the electronic device may generate the user's heart information based on peak information. For example, the electronic device may generate information about a user's blood pressure, based on the waveform of a PPG signal.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively," as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry." A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components or operations may be omitted, or one or more other components or operations may be added. Alternatively or additionally, a plurality of components (e.g., modules or programs) may be integrated into a single component. In such a case, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

According to various embodiments, in a storage medium storing commands, the commands are configured to cause at least one circuit to perform at least one operation when the commands are executed by the at least one circuit, wherein the at least one operation may include: turning on at least one light-emitting element of an electronic device; controlling at least one pixel of a spatial light modulator (SLM) of the electronic device such that the SLM outputs a first pattern by using light output from the light-emitting element; and generating photoplethysmogram (PPG) data by using a light-receiving element of the electronic device.

The invention claimed is:

1. An electronic device comprising:
a housing comprising an inner space;
a sensor structure positioned in the housing and exposed through a part of the housing; and
a processing circuit operatively connected to a light-receiving element and configured to generate photoplethysmogram (PPG) data corresponding to a PPG signal by using the light-receiving element,
wherein the sensor structure comprises:
a substantially transparent plate comprising a first surface facing a direction away from the inner space and a second surface facing a direction away from the first surface,
a support structure positioned in the inner space while facing the transparent plate,
at least one light-emitting element which is mounted on the support structure while being spaced apart from the second surface and which is inserted between the second surface and the support structure,
a spatial light modulator (SLM) disposed between the transparent plate and the light-emitting element while being spaced apart from the light-emitting element,
the light-receiving element mounted on the support structure and positioned between the second surface and the support structure while being adjacent to a side surface of the light-emitting element, and
at least one electrical path electrically connected to the SLM,
wherein the processing circuit is configured to:
receive a PPG signal based on a light output from the at least one light-emitting element,
based on a magnitude of the PPG signal, determine a position of a user's blood vessel, and
control a pattern of the SLM so that the light output from the at least one light-emitting element is output to the position of the blood vessel.

2. The electronic device of claim 1, wherein:
the light-receiving element comprises a light-receiving surface,
the light-emitting element comprises a light-emitting surface,
the light-receiving surface is closer to the second surface than the light-emitting surface is, and
the light-receiving surface is closer to the second surface than the SLM is.

3. The electronic device of claim 1,
wherein the SLM is spaced apart from the second surface, and
wherein the SLM is configured to modulate at least one of an amplitude or a phase of light emitted from the light-emitting element.

4. The electronic device of claim 1,
wherein the support structure comprises a printed circuit board (PCB), and
wherein the electrical path is connected to the printed circuit board.

5. The electronic device of claim 1, further comprising at least one light-receiving element mounted on the support structure and positioned between the second surface and the support structure while being adjacent to a side surface of the light-emitting element.

6. The electronic device of claim 1, further comprising a partition wall mounted on the support structure and positioned between the light-emitting element and the light-receiving element,
wherein a first surface of the partition wall is positioned under the second surface.

7. The electronic device of claim 1, wherein the processing circuit is further configured to generate the PPG data corresponding to the PPG signal by using the light-receiving element while controlling the pattern of the SLM.

8. The electronic device of claim 1, wherein the processing circuit is further configured to:
based on the pattern of the SLM, control to output first light having a first amplitude or a first phase.

9. The electronic device of claim 1, wherein the processing circuit is further configured to perform a random search for the pattern of the SLM.

10. The electronic device of claim 1, wherein the processing circuit is further configured to:
control to output second light having a second amplitude or a second phase to reduce scattering of the light.

11. The electronic device of claim 1, wherein the processing circuit is further configured to:
control to change the pattern of the SLM to a shifted pattern, and
generate new PPG data corresponding to a new PPG signal by using the light-receiving element.

12. The electronic device of claim 1, wherein the processing circuit is further configured to:
control to change the pattern of the SLM to a pattern with a phase gradient, and
generate new PPG data corresponding to a new PPG signal by using the light-receiving element.

13. The electronic device of claim 1, wherein the SLM is attached to the transparent plate.

14. A method for biometric information detection using a spatial light modulator (SLM) of an electronic device, the method comprising:
turning on at least one light-emitting element of the electronic device;
controlling at least one pixel of the SLM of the electronic device such that the SLM outputs a first pattern by using light output from the light-emitting element; and
generating photoplethysmogram (PPG) data corresponding to a PPG signal by using a light-receiving element of the electronic device,
wherein the method is further comprising:
receiving a PPG signal based on a light output from the at least one light-emitting element;
based on a magnitude of the PPG signal, determining a position of a user's blood vessel; and
controlling a pattern of the SLM so that the light output from the at least one light-emitting element is output to the position of the blood vessel.

15. A storage medium storing instructions, wherein the instructions are configured to cause at least one circuit to perform at least one operation when the instructions are executed by the at least one circuit,
wherein the at least one operation comprises:
turning on at least one light-emitting element of an electronic device;
controlling at least one pixel of a spatial light modulator (SLM) of the electronic device such that the SLM outputs a first pattern by using light output from the light-emitting element; and
generating photoplethysmogram (PPG) data corresponding to a PPG signal by using a light-receiving element of the electronic device,
wherein the at least one operation is further comprising:
receiving a PPG signal based on a light output from the at least one light-emitting element;
based on a magnitude of the PPG signal, determining a position of a user's blood vessel; and
controlling a pattern of the SLM so that the light output from the at least one light-emitting element is output to the position of the blood vessel.

* * * * *